US009255866B2

(12) United States Patent
Dirckx et al.

(10) Patent No.: US 9,255,866 B2
(45) Date of Patent: Feb. 9, 2016

(54) MIXING OF FLUIDS IN FLUIDIC SYSTEMS

(71) Applicant: OPKO Diagnostics, LLC, Woburn, MA (US)

(72) Inventors: Matthew Dirckx, Somerville, MA (US); Vincent Linder, Tewksbury, MA (US); Jason Taylor, Windham, NH (US)

(73) Assignee: OPKO Diagnostics, LLC, Woburn, MA (US)

( * ) Notice: Subject to any disclaimer, the term of this patent is extended or adjusted under 35 U.S.C. 154(b) by 0 days.

(21) Appl. No.: 14/446,828

(22) Filed: Jul. 30, 2014

(65) Prior Publication Data

US 2014/0342350 A1 Nov. 20, 2014

Related U.S. Application Data

(63) Continuation of application No. 14/175,044, filed on Feb. 7, 2014.

(60) Provisional application No. 61/778,905, filed on Mar. 13, 2013.

(51) Int. Cl.
*G01N 1/38* (2006.01)
*B01F 5/00* (2006.01)
(Continued)

(52) U.S. Cl.
CPC .. *G01N 1/38* (2013.01); *B01F 3/04* (2013.01); *B01F 3/08* (2013.01); *B01F 5/0085* (2013.01);
(Continued)

(58) Field of Classification Search
CPC .......................... B01L 2200/0673; G01N 1/38
USPC ............................... 436/501; 435/5
See application file for complete search history.

(56) References Cited

U.S. PATENT DOCUMENTS 3,735,640 A 5/1973 Chizhov et al.
4,318,994 A 3/1982 Meyer et al.
(Continued)

FOREIGN PATENT DOCUMENTS

CN 1254845 A 5/2000
DE 101 15 474 A1 10/2002
(Continued)

OTHER PUBLICATIONS

International Search Report and Written Opinion for PCT/US2014/015243 mailed Jun. 4, 2014.
(Continued)

*Primary Examiner* — Christopher A Hixson
*Assistant Examiner* — Emily Berkeley
(74) *Attorney, Agent, or Firm* — Wolf, Greenfield & Sacks, P.C.

(57) ABSTRACT

Fluidic devices and methods associated with mixing of fluids in fluidic devices are provided. In some embodiments, a method may involve the mixing of two or more fluids in a channel segment of a fluidic device. The fluids may be in the form of, for example, at least first, second and third fluid plugs, composed of first, second, and third fluids, respectively. The second fluid may be immiscible with the first and third fluids. In certain embodiments, the fluid plugs may be flowed in series in the channel segment, e.g., in linear order, causing the first and third fluids to mix without the use of active components such as mixers. The mixing of fluids in a channel segment as described herein may allow for improved performance and simplification in the design and operations of fluidic devices that rely on mixing of fluids.

26 Claims, 12 Drawing Sheets

(51) Int. Cl.
  *B01F 13/00* (2006.01)
  *B01L 3/00* (2006.01)
  *G01N 35/08* (2006.01)
  *B01F 3/04* (2006.01)
  *B01F 3/08* (2006.01)

(52) U.S. Cl.
  CPC ......... *B01F 13/0071* (2013.01); *B01F 13/0084* (2013.01); *B01L 3/502784* (2013.01); *G01N 35/08* (2013.01); B01L 3/502746 (2013.01); B01L 2200/16 (2013.01); B01L 2300/0816 (2013.01); B01L 2300/0867 (2013.01); B01L 2300/161 (2013.01); B01L 2400/0487 (2013.01); B01L 2400/0694 (2013.01); B01L 2400/084 (2013.01); G01N 2001/386 (2013.01)

(56) References Cited

U.S. PATENT DOCUMENTS

| | | | |
|---|---|---|---|
| 4,517,302 A | 5/1985 | Saros | |
| 4,963,498 A | 10/1990 | Hillman et al. | |
| 5,051,237 A | 9/1991 | Grenner et al. | |
| 5,219,762 A | 6/1993 | Katamine et al. | |
| 5,268,147 A | 12/1993 | Zabetakis et al. | |
| 5,286,454 A | 2/1994 | Nilsson et al. | |
| 5,376,252 A | 12/1994 | Ekström et al. | |
| 5,478,751 A | 12/1995 | Oosta et al. | |
| 5,486,335 A | 1/1996 | Wilding et al. | |
| 5,571,410 A | 11/1996 | Swedberg et al. | |
| 5,635,358 A | 6/1997 | Wilding et al. | |
| 5,637,469 A | 6/1997 | Wilding et al. | |
| 5,726,026 A | 3/1998 | Wilding et al. | |
| 5,731,212 A | 3/1998 | Gavin et al. | |
| 5,783,148 A | 7/1998 | Cottingham et al. | |
| 5,842,787 A | 12/1998 | Kopf-Sill et al. | |
| 5,866,345 A | 2/1999 | Wilding et al. | |
| 5,876,675 A | 3/1999 | Kennedy | |
| 5,942,443 A | 8/1999 | Parce et al. | |
| 5,955,028 A | 9/1999 | Chow | |
| 5,957,579 A | 9/1999 | Kopf-Sill et al. | |
| 6,019,944 A | 2/2000 | Buechler | |
| 6,042,709 A | 3/2000 | Parce et al. | |
| 6,046,056 A | 4/2000 | Parce et al. | |
| 6,103,199 A | 8/2000 | Bjornson et al. | |
| 6,136,272 A | 10/2000 | Weigl et al. | |
| 6,146,489 A | 11/2000 | Wirth | |
| 6,146,589 A | 11/2000 | Chandler | |
| 6,168,948 B1 | 1/2001 | Anderson et al. | |
| 6,176,962 B1 | 1/2001 | Soane et al. | |
| 6,184,029 B1 | 2/2001 | Wilding et al. | |
| 6,186,660 B1 | 2/2001 | Kopf-Sill et al. | |
| 6,214,560 B1 | 4/2001 | Yguerabide et al. | |
| 6,238,538 B1 | 5/2001 | Parce et al. | |
| 6,241,560 B1 | 6/2001 | Furusawa et al. | |
| 6,251,343 B1 | 6/2001 | Dubrow et al. | |
| 6,274,337 B1 | 8/2001 | Parce et al. | |
| 6,296,020 B1 | 10/2001 | McNeely et al. | |
| 6,331,439 B1 | 12/2001 | Cherukuri et al. | |
| 6,333,200 B1 | 12/2001 | Kaler et al. | |
| 6,361,958 B1 | 3/2002 | Shieh et al. | |
| 6,413,782 B1 | 7/2002 | Parce et al. | |
| 6,416,642 B1 | 7/2002 | Alajoki et al. | |
| 6,429,025 B1 | 8/2002 | Parce et al. | |
| 6,432,720 B2 | 8/2002 | Chow | |
| 6,479,299 B1 | 11/2002 | Parce et al. | |
| 6,488,872 B1 | 12/2002 | Beebe et al. | |
| 6,488,894 B1 | 12/2002 | Miethe et al. | |
| 6,488,896 B2 | 12/2002 | Weigl et al. | |
| 6,517,234 B1 | 2/2003 | Kopf-Sill et al. | |
| 6,524,656 B2 | 2/2003 | Even et al. | |
| 6,551,841 B1 | 4/2003 | Wilding et al. | |
| 6,610,499 B1 | 8/2003 | Fulwyler et al. | |
| 6,613,512 B1 | 9/2003 | Kopf-Sill et al. | |
| 6,613,525 B2 | 9/2003 | Nelson et al. | |
| 6,620,625 B2 | 9/2003 | Wolk et al. | |
| 6,632,619 B1 | 10/2003 | Harrison et al. | |
| 6,638,482 B1 | 10/2003 | Ackley et al. | |
| 6,656,430 B2 | 12/2003 | Sheppard, Jr. et al. | |
| 6,669,831 B2 | 12/2003 | Chow et al. | |
| 6,705,357 B2 | 3/2004 | Jeon et al. | |
| 6,709,869 B2 | 3/2004 | Mian et al. | |
| 6,716,620 B2 | 4/2004 | Bashir et al. | |
| 6,742,661 B1 | 6/2004 | Schulte et al. | |
| 6,761,962 B2 | 7/2004 | Bentsen et al. | |
| 6,780,584 B1 | 8/2004 | Edman et al. | |
| 6,794,197 B1 | 9/2004 | Indermuhle et al. | |
| 6,818,184 B2 | 11/2004 | Fulwyler et al. | |
| 6,827,095 B2 | 12/2004 | O'Connor et al. | |
| 6,828,143 B1 | 12/2004 | Bard | |
| 6,830,936 B2 | 12/2004 | Anderson et al. | |
| 6,858,185 B1 | 2/2005 | Kopf-Sill et al. | |
| 6,878,271 B2 | 4/2005 | Gilbert et al. | |
| 6,878,755 B2 | 4/2005 | Singh et al. | |
| 6,949,377 B2 | 9/2005 | Ho | |
| 6,953,550 B2 | 10/2005 | Sheppard, Jr. et al. | |
| 6,982,787 B1 | 1/2006 | Wapner et al. | |
| 6,989,128 B2 | 1/2006 | Alajoki et al. | |
| 7,005,292 B2 | 2/2006 | Wilding et al. | |
| 7,015,046 B2 | 3/2006 | Wohlstadter et al. | |
| 7,018,830 B2 | 3/2006 | Wilding et al. | |
| 7,067,263 B2 | 6/2006 | Parce et al. | |
| 7,087,148 B1 | 8/2006 | Blackburn et al. | |
| 7,091,048 B2 | 8/2006 | Parce et al. | |
| 7,160,423 B2 | 1/2007 | Chien et al. | |
| 7,276,330 B2 | 10/2007 | Chow et al. | |
| 7,540,475 B2 | 6/2009 | Stenkamp et al. | |
| 7,816,411 B2 | 10/2010 | Tonkovich et al. | |
| 8,030,057 B2 | 10/2011 | Linder et al. | |
| 8,075,778 B2 | 12/2011 | Guenther et al. | |
| 8,202,492 B2 | 6/2012 | Linder et al. | |
| 8,221,700 B2 | 7/2012 | Steinmiller et al. | |
| 8,222,049 B2 | 7/2012 | Linder et al. | |
| 8,389,272 B2 | 3/2013 | Linder et al. | |
| 8,409,527 B2 | 4/2013 | Linder et al. | |
| 8,475,737 B2 | 7/2013 | Linder et al. | |
| 8,480,975 B2 | 7/2013 | Steinmiller et al. | |
| 8,501,416 B2 | 8/2013 | Linder et al. | |
| 8,567,425 B2 | 10/2013 | Tan et al. | |
| 8,580,569 B2 | 11/2013 | Linder et al. | |
| 8,591,829 B2 | 11/2013 | Taylor et al. | |
| 8,765,062 B2 | 7/2014 | Linder et al. | |
| 2002/0001818 A1 | 1/2002 | Brock | |
| 2002/0019059 A1 | 2/2002 | Chow et al. | |
| 2002/0071788 A1 | 6/2002 | Fujii et al. | |
| 2002/0092767 A1 | 7/2002 | Bjornson et al. | |
| 2002/0142618 A1 | 10/2002 | Parce et al. | |
| 2002/0199094 A1 | 12/2002 | Strand et al. | |
| 2003/0012697 A1 | 1/2003 | Hahn et al. | |
| 2003/0040105 A1 | 2/2003 | Sklar et al. | |
| 2003/0082081 A1 | 5/2003 | Fouillet et al. | |
| 2003/0118486 A1 | 6/2003 | Zhou et al. | |
| 2003/0124623 A1 | 7/2003 | Yager et al. | |
| 2003/0138969 A1 | 7/2003 | Jakobsen et al. | |
| 2003/0185713 A1 | 10/2003 | Leonard et al. | |
| 2003/0207328 A1 | 11/2003 | Yguerabide et al. | |
| 2004/0077074 A1 | 4/2004 | Ackley et al. | |
| 2004/0115094 A1 | 6/2004 | Gumbrecht et al. | |
| 2004/0115731 A1 | 6/2004 | Hansen et al. | |
| 2004/0195728 A1 | 10/2004 | Slomski et al. | |
| 2004/0228771 A1 | 11/2004 | Zhou et al. | |
| 2004/0259268 A1 | 12/2004 | Jacobs et al. | |
| 2005/0118073 A1 | 6/2005 | Facer et al. | |
| 2005/0161669 A1 | 7/2005 | Jovanovich et al. | |
| 2005/0221281 A1 | 10/2005 | Ho | |
| 2005/0238545 A1 | 10/2005 | Parce et al. | |
| 2005/0255003 A1 | 11/2005 | Summersgill et al. | |
| 2005/0272159 A1 | 12/2005 | Ismagilov et al. | |
| 2006/0002827 A1 | 1/2006 | Curcio et al. | |
| 2006/0094119 A1* | 5/2006 | Ismagilov et al. | 436/53 |
| 2006/0147909 A1 | 7/2006 | Rarbach et al. | |
| 2006/0257992 A1 | 11/2006 | McDevitt et al. | |

(56) References Cited

U.S. PATENT DOCUMENTS

| | | |
|---|---|---|
| 2006/0275852 A1 | 12/2006 | Montagu |
| 2007/0048189 A1 | 3/2007 | Cox et al. |
| 2007/0195127 A1 | 8/2007 | Ahn et al. |
| 2007/0298433 A1 | 12/2007 | Sia et al. |
| 2008/0085219 A1 | 4/2008 | Beebe et al. |
| 2008/0248590 A1 | 10/2008 | Gulliksen et al. |
| 2008/0280365 A1 | 11/2008 | Grumann et al. |
| 2009/0075390 A1* | 3/2009 | Linder .................. A61L 2/0082 436/161 |
| 2009/0282978 A1 | 11/2009 | Jensen et al. |
| 2010/0122899 A1 | 5/2010 | Hartman et al. |
| 2010/0158756 A1* | 6/2010 | Taylor et al. .................... 422/69 |
| 2010/0208543 A1 | 8/2010 | Takahashi et al. |
| 2010/0209916 A1 | 8/2010 | Zon |
| 2010/0216964 A1 | 8/2010 | Zech et al. |
| 2011/0103176 A1 | 5/2011 | Van Dam et al. |
| 2011/0120562 A1 | 5/2011 | Tan et al. |
| 2011/0171748 A1 | 7/2011 | Cox et al. |
| 2011/0256551 A1 | 10/2011 | Linder et al. |
| 2012/0241013 A1 | 9/2012 | Linder et al. |
| 2013/0157286 A1 | 6/2013 | Linder et al. |
| 2013/0236375 A1 | 9/2013 | Tan et al. |
| 2013/0252321 A1 | 9/2013 | Steinmiller et al. |
| 2013/0330748 A1 | 12/2013 | Linder et al. |
| 2014/0023565 A1 | 1/2014 | Taylor et al. |
| 2014/0038166 A1 | 2/2014 | Linder et al. |
| 2014/0038167 A1 | 2/2014 | Linder et al. |
| 2014/0093866 A1 | 4/2014 | Tan et al. |
| 2014/0272935 A1 | 9/2014 | Linder et al. |

FOREIGN PATENT DOCUMENTS

| | | |
|---|---|---|
| EP | 0 110 771 B1 | 3/1988 |
| EP | 0 281 201 A1 | 9/1988 |
| EP | 0 430 248 A2 | 6/1991 |
| EP | 0 481 020 B1 | 4/1992 |
| EP | 0 643 307 A1 | 3/1995 |
| EP | 1 054 259 A1 | 11/2000 |
| EP | 1 992 404 A2 | 11/2002 |
| EP | 1 946 830 A1 | 7/2008 |
| EP | 2 071 026 A1 | 6/2009 |
| JP | 2000-019175 A | 1/2000 |
| JP | 2001-000197 A | 1/2001 |
| JP | 2001-004628 A | 1/2001 |
| JP | 2002-236131 A | 8/2002 |
| JP | 2002-527750 A | 8/2002 |
| JP | 2002-536640 A | 10/2002 |
| JP | 2002-340897 A | 11/2002 |
| JP | 2003-075444 A | 3/2003 |
| JP | 2003-223674 A | 8/2003 |
| JP | 2006-524815 A | 11/2006 |
| JP | 2008-139296 A | 6/2008 |
| WO | WO 91/01003 A | 1/1991 |
| WO | WO 00/22434 A1 | 4/2000 |
| WO | WO 00/46595 A1 | 8/2000 |
| WO | WO 02/22250 A2 | 3/2002 |
| WO | WO 03/054513 A2 | 7/2003 |
| WO | WO 03/062826 A2 | 7/2003 |
| WO | WO 2004/042341 A2 | 5/2004 |
| WO | WO 2004/087951 A2 | 10/2004 |
| WO | WO 2004/087951 A3 | 10/2004 |
| WO | WO 2004/097419 A1 | 11/2004 |
| WO | WO 2005/056186 A1 | 6/2005 |
| WO | WO 2005/072858 A1 | 8/2005 |
| WO | WO 2006/018044 A1 | 2/2006 |
| WO | WO 2006/056787 A1 | 6/2006 |
| WO | WO 2006/113727 A2 | 10/2006 |
| WO | WO 2008/118098 A1 | 10/2008 |
| WO | WO 2008/123112 A1 | 10/2008 |

OTHER PUBLICATIONS

International Search Report and Written Opinion for PCT/US2005/003514 mailed May 13, 2005.

International Preliminary Report on Patentability for PCT/US2005/003514 mailed Aug. 3, 2006.

Ahn et al., Disposable Smart Lab on a Chip for Point-of-Care Clinical Diagnostics, Proceedings of the IEEE. 2004; 92(1):154-173.

Andersson et al., Micromachined Flow-Through Filter-Chamber for Chemical Reactions on Beads. Sensors and Actuators. 2000; B67:203-208.

Atencia et al., Capillary inserts in microcirculatory systems. Lab Chip. Apr. 2006;6(4):575-7. Epub Jan. 20, 2006.

Atencia et al., Steady flow generation in microcirculatory systems. Lab Chip. Apr. 2006;6(4):567-74. Epub Jan. 20, 2006.

Dardion, et al., "Chemical Sensing Using an Integrated Microfluidic System Based on the Berthelot Reaction", *Sensors and Actuators B*, vol. 76, pp. 235-243 (2001).

Dodge et al., Electrokinetically driven microfluidic chips with surface-modified chambers for heterogeneous immunoassays. Anal Chem. Jul. 15, 2001;73(14):3400-9.

Fredrickson et al., Macro-to-micro interfaces for microfluidic devices. Lab Chip. Dec. 2004;4(6):526-33. Epub Nov. 10, 2004.

Grodzinski et al., A Modular Microfluidic System for Cell Pre-concentration and Genetic Sample Preparation. Biomedical Microdevices. 2003;5(4):303-310.

Guo et al, Valve-based microfluidic droplet micromixer and mercury (II) ion detection. Sensors and Actuators. 2011; 172: 546-51.

Harries et al, A numerical model for segmented flow in a microreactor. Int J Heat and Mass Transfer. 2003; 46: 3313-22.

Juncker et al., Autonomous microfluidic capillary system. Anal Chem. Dec. 15, 2002;74(24):6139-44.

Kumar et al. Segmented flow synthesis of Ag nanoparticles in spiral microreactor: Role of continuous and disperzsed phase. Chem Eng J. 2012; 192: 357-68. With Supporting Information.

Linder et al., Reagent-loaded cartridges for valveless and automated fluid delivery in microfluidic devices. Anal Chem. Jan. 1, 2005;77(1):64-71.

Moorthy et al., Microfluidic Tectonics Platform: A colorimetric, disposable botulinum toxin enzyme-linked immunosorbent assay system. Electrophoresis. Jun. 2004;25(10-11):1705-13.

Nguyen et al., An analytical model for mixing based on time-interleaved sequential segmentation. Microfluid Nanofluid. 2005; 1: 373-5.

Nguyen et al., Modelling, fabrication and characterization of a polymeric micromixer based on sequential segmentation. Biomed Microdevices. Jun. 2006;8(2):133-9.

Obeid et al., Microfabricated device for DNA and RNA amplification by continuous-flow polymerase chain reaction and reverse transcription-polymerase chain reaction with cycle number selection. Anal Chem. Jan. 15, 2003;75(2):288-95.

Proceedings of uTAS 2004, 8th International Conference on Miniaturized Systems in Chemistry and Life Sciences, Sep. 26-30, Malmo, Sweden, Edited by Thomas Laurell, Johan Nilsson, Klavs Jensen, D. Jed Harrison, Jorg P. Kutter, The Royal Society of Chemistry, pp. 1-135 (2004).

Shui et al., Multiphase flow in microfluidic systems—control and applications of droplets and interfaces. Adv Colloid Interface Sci. May 31, 2007;133(1):35-49. Epub Mar. 16, 2007.

Sia et al., An integrated approach to a portable and low-cost immunoassay for resource-poor settings. Angew Chem Int Ed Engl. Jan. 16, 2004;43(4):498-502.

Sia et al., Microfluidic devices fabricated in poly(dimethylsiloxane) for biological studies. Electrophoresis. Nov. 2003;24(21):3563-76.

Song et al., A microfluidic system for controlling reaction networks in time. Angew Chem Int Ed. 2003;42(7):767-772.

Weigl et al., Lab-on-a-Chip for Drug Development. Adv Drug Deliv Rev. Feb. 24, 2003;55(3):349-77.

\* cited by examiner

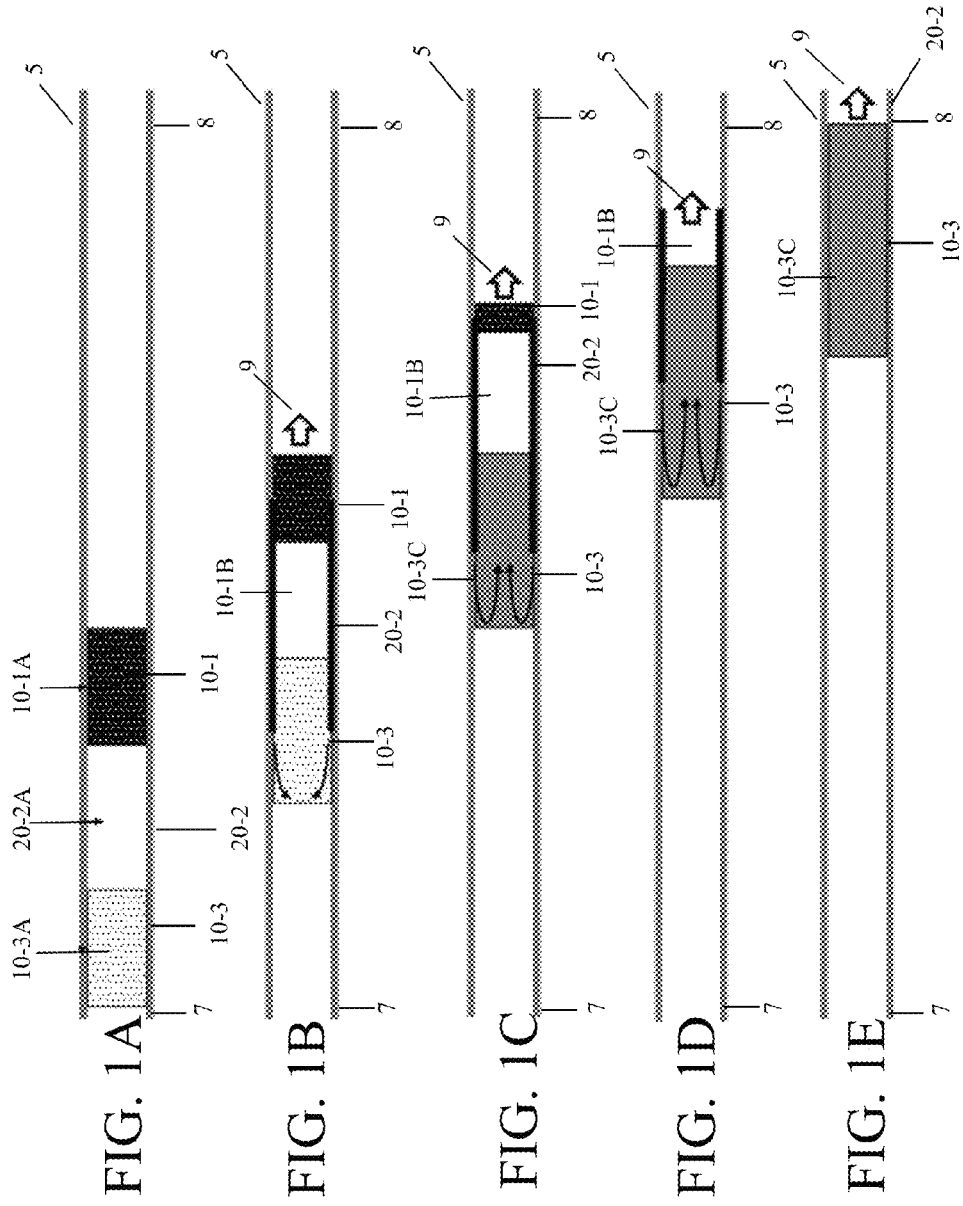

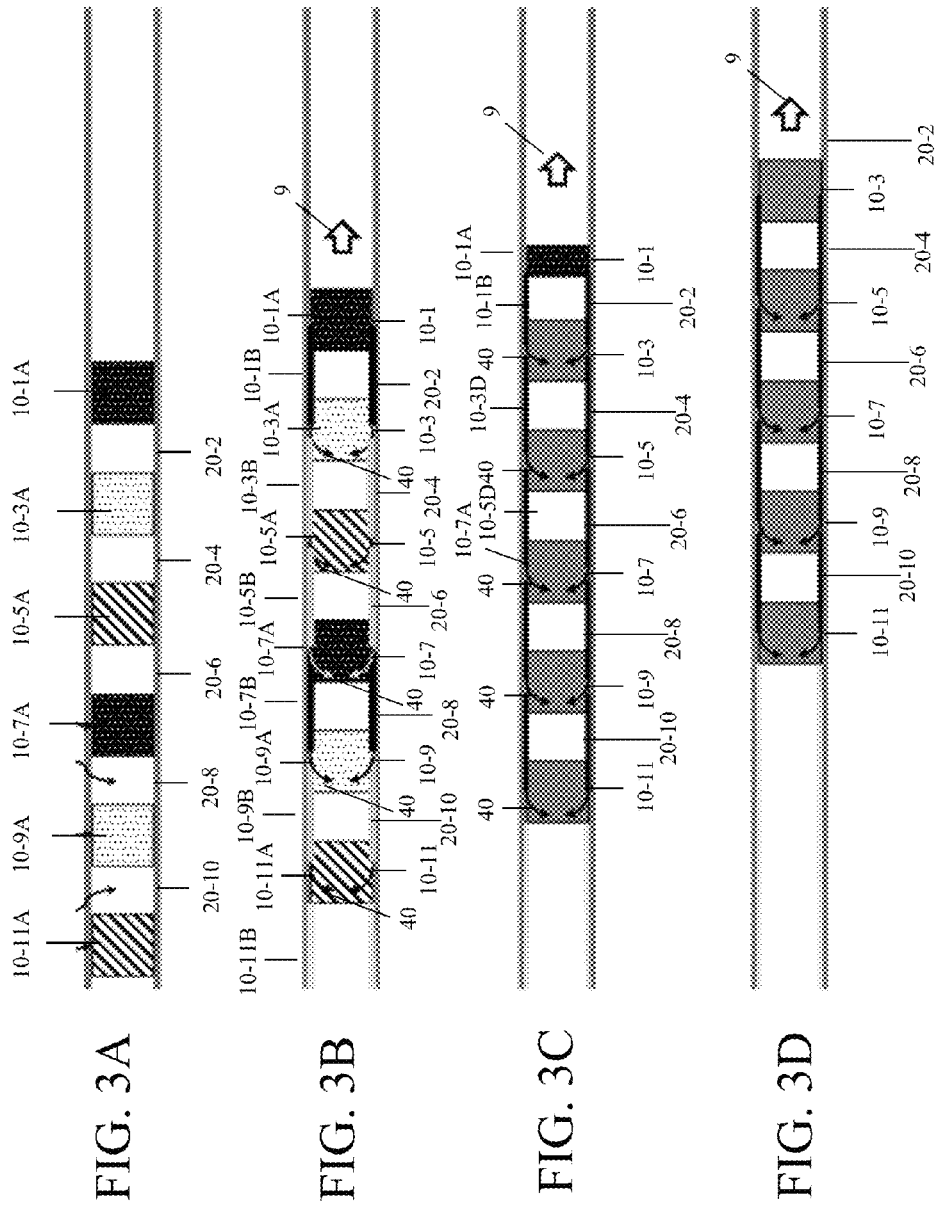

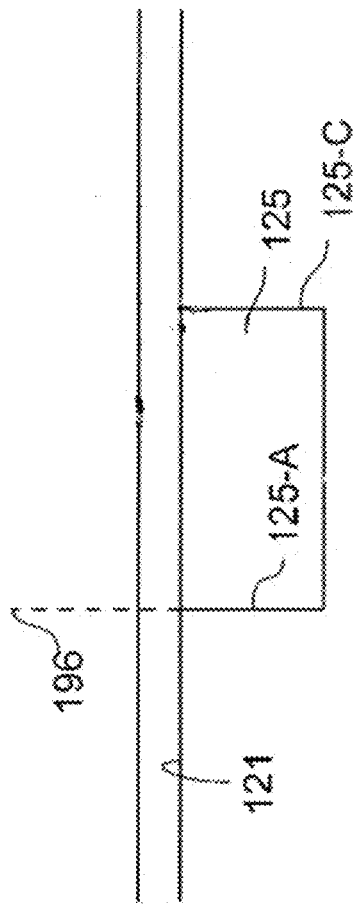
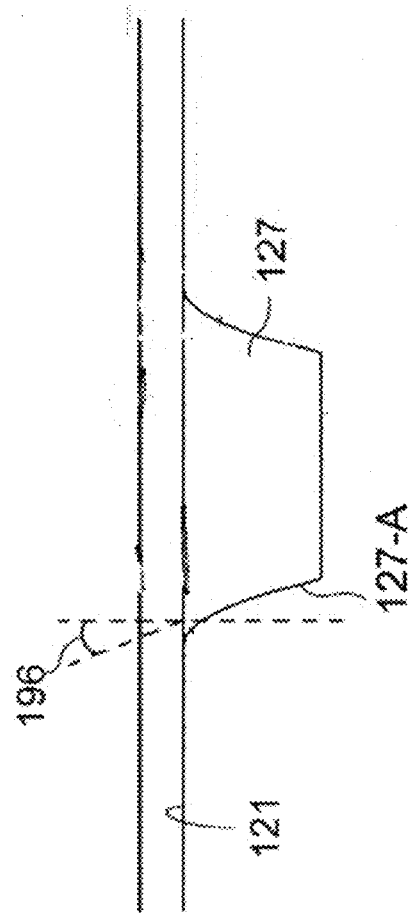
FIG. 5A
FIG. 5B

MIXING OF FLUIDS IN FLUIDIC SYSTEMS

RELATED APPLICATIONS

The present application is a continuation of U.S. patent application Ser. No. 14/175,044, filed Feb. 7, 2014, and entitled "Mixing of Fluids in Fluidic Systems," which claims priority under 35 U.S.C. §119(e) to U.S. Provisional Patent Application No. 61/778,905, filed Mar. 13, 2013, and entitled "Mixing of Fluids in Fluidic Systems," each of which is incorporated herein by reference in its entirety.

FIELD OF INVENTION

The present embodiments relate generally to methods for flowing fluids in fluidic devices, and more specifically, to methods that involve the mixing of fluids.

BACKGROUND

The manipulation of fluids plays an important role in fields such as chemistry, microbiology and biochemistry. These fluids may include liquids or gases and may provide reagents, solvents, reactants, or rinses to chemical or biological processes. While various fluidic (e.g., microfluidic) methods and devices, such as microfluidic assays, can provide inexpensive, sensitive and accurate analytical platforms, fluid manipulations—such as the mixture of multiple fluids, sample introduction, introduction of reagents, storage of reagents, separation of fluids, collection of waste, extraction of fluids for off-chip analysis, and transfer of fluids from one chip to the next—can add a level of cost and sophistication. Accordingly, advances in the field that could reduce costs, simplify use, and/or improve fluid manipulations in microfluidic systems would be beneficial.

SUMMARY OF THE INVENTION

Methods for flowing fluids in fluidic devices, and related components, devices and systems associated therewith are provided. The subject matter of this application involves, in some cases, interrelated methods, alternative solutions to a particular problem, and/or a plurality of different uses of fluids and devices.

In one set of embodiment, a series of methods are provided. In one embodiment, a method comprises flowing in series in a channel a first fluid plug comprising a first fluid, a second fluid plug comprising a second fluid, and a third fluid plug comprising a third fluid. The first fluid plug has a first volume. The second fluid plug is positioned between the first and third fluid plugs and the second fluid is immiscible with each of the first and third fluids. The method further comprises reducing the first volume of the first fluid plug by at least 50% and combining at least a portion of the first fluid into the third fluid plug so as to mix at least portions of the first and third fluids.

In another embodiment, a method comprises flowing in series in a channel a first fluid plug comprising a first fluid, a second fluid plug comprising a second fluid, and a third fluid plug comprising a third fluid. The second fluid is immiscible with each of the first and third fluids and the second fluid plug is positioned between the first and third fluid plugs. The first fluid comprises a first component for a chemical and/or biological reaction and the third fluid comprises a second component for a chemical and/or biological reaction. The first component is different from the second component. The method further comprises depositing at least a portion of the first fluid on a wall of the channel during the flowing step and combining at least a portion of the first fluid deposited on the wall of the channel into the third fluid plug so as to mix at least portions of the first and third fluids.

In one embodiment, a method comprises flowing in series in a channel a first fluid plug comprising a first fluid, a second fluid plug comprising a second fluid, and a third fluid plug comprising a third fluid. The first fluid comprises a first component for a chemical and/or biological reaction and the third fluid comprises a second component for a chemical and/or biological reaction. The second fluid is immiscible with the first and third fluids, and the second fluid plug is positioned between the first and third fluid plugs. The method further comprises combining at least a portion of the first fluid into the third fluid plug so as to mix at least portions of the first and third fluids and performing one or more chemical and/or biological reactions involving each of the first and second components.

In another embodiment, a method comprises providing a fluidic device containing a first fluid and a second fluid. The first and second fluids are stored and sealed in the fluidic device and kept separate from one another during storage. The method further comprises unsealing the fluidic device and flowing in series in a channel a series of fluid plugs comprising a first fluid plug comprising the first fluid, a second fluid plug comprising the second fluid, and a third fluid plug comprising a third fluid. The third fluid plug is positioned between the first and second fluid plugs and the third fluid is immiscible with the first and second fluids. The method further comprises combining at least a portion of the first fluid into the second fluid plug so as to mix at least portions of the first and second fluids.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1E show methods of mixing fluid plugs in a channel segment according to one set of embodiments;

FIGS. 3A-3D show methods of mixing of at least three different fluid plugs in a channel segment according to one set of embodiments;

FIGS. 5A-5B show cross-sectional dimensions of a channel segment according to one set of embodiments;

DETAILED DESCRIPTION

Figure 2A:
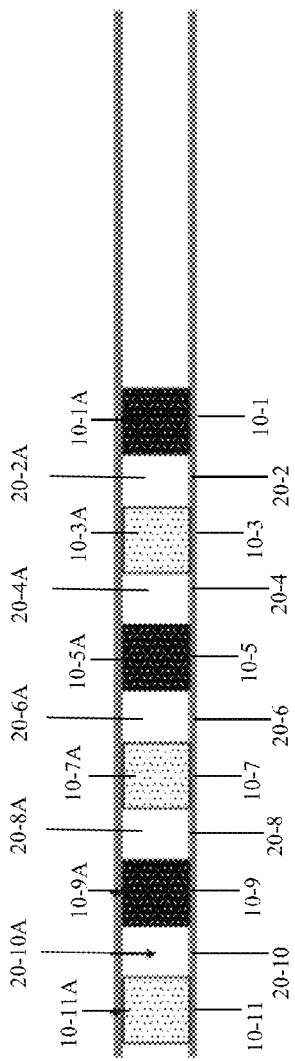
FIGS. 2A-2D show methods of mixing multiple fluid plugs simultaneously in a channel segment according to one set of embodiments.

Fluidic devices and methods associated with mixing of fluids in fluidic devices are provided. In some embodiments, a method may involve the mixing of two or more fluids in a channel segment of a fluidic device. Mixing may take place when at least some of the fluids are positioned series in the channel segment. The fluids may be in the form of, for example, at least first, second and third fluid plugs, composed of first, second, and third fluids, respectively. The second fluid may be immiscible with the first and third fluids. In certain embodiments, the fluid plugs may be flowed in series in the channel segment, e.g., in linear order. As the first fluid plug flows in the channel segment, at least a portion of the first fluid may be removed from the first plug, thereby reducing the volume of the first fluid plug. For instance, portions of the first fluid may be deposited on the wall of the channel during this flowing step. As the third fluid plug flows in the channel, the third fluid may mix with portions of the deposited fluid to form a mixture of the first and third fluids in the third fluid plug. The mixing of fluids in a channel segment as described herein may allow for improved performance and simplification in the design and operations of fluidic devices that rely on mixing of fluids. For example, in some embodiments active components such as mixers are not needed in the fluidic device.

An example of a method of mixing in a channel segment is shown in FIGS. 1A-E. As shown illustratively in FIG. 1A, a channel segment 5, including an upstream portion 7 and a downstream portion 8, may contain a first fluid plug 10-1 containing a first fluid 10-1A, a second fluid plug 20-2 containing a second fluid 20-2A, and a third fluid plug 10-3, containing a third fluid 10-3A. As shown illustratively in this figure, the second fluid plug may be positioned between and directly adjacent to the first and third fluid plugs. In some embodiments, the second fluid may be immiscible with the first and third fluids, while the first and third fluids may optionally be miscible with one another. For example, the second fluid may be a gas (e.g., air) and the first and third fluids may be liquids. Other fluid plugs may also be present in the channel segment as described in more detail below.

As used herein, when a fluid or fluid plug is referred to as being "adjacent" another fluid or fluid plug, it can be directly adjacent the fluid or fluid plug, or an intervening fluid or fluid plug also may be present. A fluid or fluid plug that is "directly adjacent" or "in contact with" another fluid or fluid plug means that no intervening fluid or fluid plug is present.

As shown in FIG. 1B, the fluids may be flowed in series, e.g., from upstream to downstream in the direction of arrow 9. The channel segment may be configured such that the flowing of the fluid plugs leads to the reduction of volume of the first fluid plug. For example, at least a portion of the first fluid (e.g., fluid portion 10-1B) may deposit onto a wall of the channel segment during fluid flow. Various channel configurations and methods for reducing the volume of the first fluid plug are described in more detail herein. In certain embodiments, in which the second fluid is immiscible with the first fluid, fluid portion 10-1B does not combine with the second fluid plug and as the second fluid plug flows in the channel segment. In embodiments in which the third fluid is miscible with the first fluid, the first and third fluids may combine to form a mixture 10-3C of at least portions of the two fluids, as shown illustratively in FIG. 1C.

In some cases, as the first fluid plug flows, its volume may continue to reduce to a desired extent, for example, until mixture 10-3C includes a certain ratio of the first and third fluids, until a particular reduced volume of the first fluid plug has been reached, until a particular concentration of a component is present, or until a particular physical or chemical property is achieved. In some cases, the volume of the first fluid may be reduced by, for example, at least 50% as shown in FIG. 1C. In other cases, as shown illustratively in FIG. 1D, the entire volume of the first fluid plug may be reduced, such that only the second and third fluid plugs remain. The third fluid plug may then mix with the entire volume of the first fluid, as shown in FIG. 1E.

In some embodiments, the first and third fluids may contain a first and second component, respectively, for a chemical and/or biological reaction. In some cases, the first and second components are the same. In other embodiments, the first and second components are different. In some instances, a chemical and/or biological reaction involving the first and second components may be performed within the third fluid plug containing the mixture of the first and third fluids. For example, the first fluid may contain a silver salt and the third fluid may contain a reducing agent. The mixture of the first and third fluid may react with a reagent (e.g., gold colloids) to form detectable species (e.g., a silver film or particles that may be detected, for example, optically), as described in more detail below. Additional examples of chemical and/or biological reactions are described in more detail below. In certain embodiments, one or more fluid plugs contains a rinse solution. Other types of fluids are also possible.

As described herein, in some embodiments a fluid from a fluid plug may be deposited onto a wall of a channel (e.g., in the form a fluid portion which may be available for mixing with a fluid from another fluid plug). The fluid portion may be deposited as a film (e.g., a continuous or discontinuous film) of liquid on the wall of a channel, as fluid droplets, or in any other suitable form. The form in which deposition occurs may depend on factors such as the type of fluid being deposited, surface tension, surface energy of the channel wall, surface roughness of the channel wall, channel geometry and/or other factors. In some cases, at least a portion of the fluid deposited on the wall remains on the wall of the channel for the remainder of fluid flow. In other cases, however, substantially all of the fluid portion is combined with another fluid during subsequent fluid flow.

An example of a method of mixing several fluids in a channel segment is shown in FIGS. 2A-E. As shown in FIG. 2A, channel segment 5, including upstream portion 7 and downstream portion 8, may contain multiple fluid plugs. In some embodiments, as illustrated in FIG. 2A, the channel segment may include a first 10-1, a second 20-2, a third 10-3, a fourth 20-4, a fifth 10-5, a sixth 20-6, a seventh 10-7, an eighth 20-8, a ninth 10-9, a tenth 20-10, and an eleventh 10-11 fluid plug, which contain a first, a second, a third, a fourth, a fifth, a sixth, a seventh, an eighth, a ninth, a tenth, and an eleventh fluid, respectively. In some cases, the fluid plugs may alternate in respect to a particular property (e.g., phase, composition, viscosity, pH, volume, etc.). For example, in one set of embodiments, the odd numbered fluids shown in FIG. 2 (i.e., first, third, fifth, seventh, ninth, and eleventh) may be liquids and the even numbered fluids (i.e., second, fourth, sixth, eighth, and tenth) may be immiscible with those liquids (e.g., they may be gases). It should be understood that the labeling of "odd" or "even" fluids is for descriptive purposes only and is not intended to limit the fluids to a particular property or configuration. For instance, in other embodiments, one or more odd numbered fluids described herein may be immiscible fluids (e.g., gases) and one or more even numbered fluids may be liquids. Other configurations are also possible.

Figure 2B:
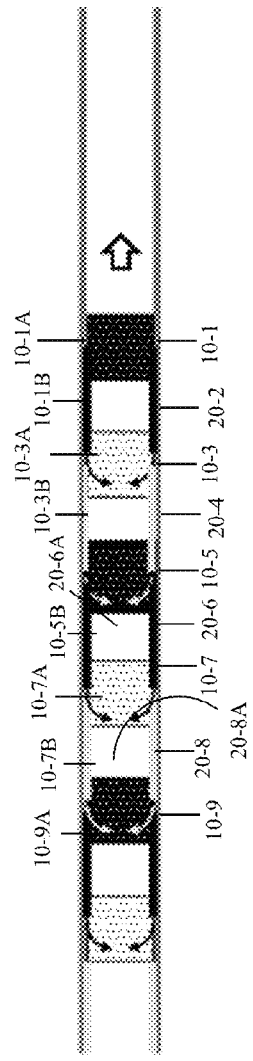

In some embodiments, the channel segment may be configured such that flowing the fluids through the channel segment results in the deposition of fluids from more than one fluid plug (e.g., odd numbered fluids) on a wall of the channel segment, as shown illustratively in FIG. 2B. This deposition may occur simultaneously or subsequently. As shown in FIG. 2B, fluid portion 10-1B may be removed from fluid 10-1A and fluid portion 10-3B may be removed from fluid 10-3A, e.g., by the fluid portions being deposited on a wall of the channel segment (e.g., dispersed along or within the channel). During flow, the fluid portions may mix with the next "like"-fluid upstream in the sequence. For instance, in embodiments in which the odd numbered fluids are miscible with each other but immiscible with the even numbered fluids, the fluid portions (formed from an odd numbered fluid) may mix with other odd numbered fluids and do not mix with the even numbered fluids. For example, fluid portion 10-5B from the fifth fluid plug may mix with the fluid in the seventh, but not the sixth, fluid plug. Simultaneously or sequentially, fluid portion 10-7B from the seventh fluid plug may mix with the fluid in the ninth fluid plug, but not the eight fluid plug.

Figure 2C:
Figure 2D:
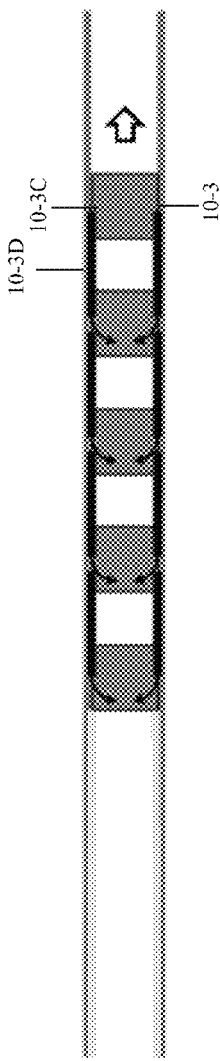
Figure 4:
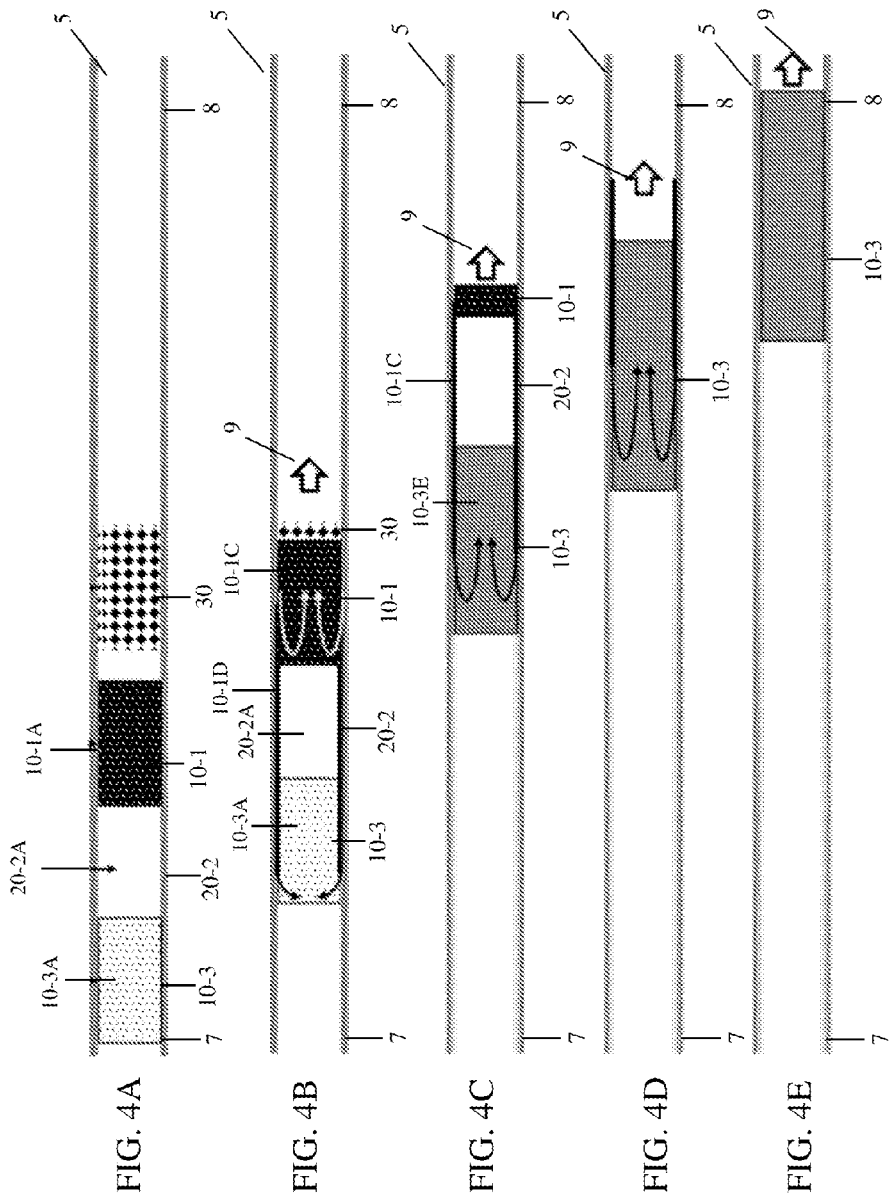
FIGS. 4A-4E show methods of mixing fluid plugs with a substantially dry reagent in a channel segment according to one set of embodiments.

In some embodiments, as the fluids flow in series, the composition (or other property such as viscosity, pH, and/or volume) of the fluid portions and each fluid in its respective fluid plug may change, as illustrated in FIG. 2C. For instance, the third fluid plug may contain fluid 10-3A at the start of the process, as shown in FIG. 2A. As the third fluid plug flows, the third fluid may mix with (and optionally react with) fluid portion 10-1B from the first fluid to form a mixture 10-3C of the first and third fluid in the third fluid plug. Subsequent fluid portions 10-3D removed from the third fluid plug may be a mixture of the first and third fluid as shown in FIG. 2C-2D. In some cases, as the fluids flow in series, the volume of the fluid in the first fluid plug may be reduced by various amounts. In certain cases, the entire volume of a fluid (e.g., the first fluid as shown illustratively in FIG. 2D) may be incorporated into one or more subsequent fluid plugs that contain fluids miscible with the fluid, such that the fluid plug is no longer present in the channel segment.

Another example of a method of mixing several fluids in a channel segment is shown in FIGS. 3A-D. As shown illustratively in FIGS. 3A-D, channel segment 5, including upstream portion 7 and downstream portion 8, may contain multiple fluid plugs that alternate in respect to particular property (e.g., phase), such that the fluid in each fluid plug is immiscible with the fluids in adjacent fluid plugs. For instance, as shown in FIG. 3A, first fluid 10-1A, third fluid 10-3A fifth fluid 10-5A, seventh fluid 10-7A, ninth fluid 10-9A, and eleventh fluid 10-11A are separated from each other by intervening fluid plugs 20-2, 20-4, 20-6, 20-8, and 20-10. The first, third, and fifth fluids may differ in a particular property (e.g., composition, viscosity, pH, volume, etc.) and the seventh, ninth, and eleventh fluids also may differ in a particular property (e.g., composition, viscosity, pH, volume, etc.). In some embodiments, the first, third, and fifth fluids may have a particular property that is substantially similar to the seventh, ninth, and eleventh fluids, respectively, although in other embodiments the particular property may differ. When flowed in the channel segment, at least one of the first, third, fifth, seventh, ninth, and eleventh fluid plugs may deposit a fluid portion (e.g., 10-1B, 10-3B, 10-5B, 10-7B, 10-9B, 10-11B, respectively) on a wall of the channel, as illustratively shown in FIG. 3B. During flow, the fluid portions may mix with the next miscible fluid upstream in the sequence, as indicated by arrows 40 shown in FIG. 3B-C.

In some embodiments, a fluid, after mixing with a fluid portion, may become substantially different from a fluid in another fluid plug with respect to at least one property (e.g., composition, viscosity, pH, volume, etc.). For instance, as shown in FIG. 3C, seventh fluid 10-7A, which may initially be substantially similar in composition to first fluid 10-1A (e.g., prior to mixing), may differ from the first fluid after mixing with a fluid portion (e.g., fluid portion 10-5B from fifth fluid 10-5A). In other embodiments, a fluid, after mixing with a fluid portion, may become substantially similar to a fluid in another fluid plug with respect to at least one property (e.g., composition, viscosity, pH, volume, etc.). For example, eleventh fluid 10-11A may become substantially similar to third fluid 10-3A after the eleventh fluid mixes with fluid portion 10-9B, which has the same composition as the third fluid.

It should be appreciated that while FIGS. 3A-3D show that mixing can occur between each "like" fluid of fluid plug (e.g., first, third, fifth, seventh, ninth, and eleventh fluids), in other embodiments, one or more such fluids/fluid plugs may be designed to not mix with another fluid, e.g., by controlling surface tension, polarity, interfacial tension, and/or other factors as described in more detail herein. For example, in one embodiment, fifth fluid plug 10-5 may be designed such that fluid 10-5A within the fluid plug is not substantially removed from the fluid plug during fluid flow. In such an embodiment, fluid portion 10-3B from the third fluid plug may flow past fluid plug 10-5 and may mix directly with fluid from seventh fluid plug 10-7. Other configurations of mixing are also possible.

In certain embodiments, a fluid plug may contain fluids from more than one fluid plug, e.g., after a mixing process described herein. During fluid flow, the fluid plug containing the multiple fluids may itself have fluid removed from it (e.g., by depositing fluid on a wall of a channel segment and/or dispersed along or within the channel) to facilitate further mixing of fluids. For example, as illustrated in FIG. 3C, the first, third, fifth, seventh, ninth, and eleventh fluid plugs may contain miscible fluids. During flow, the first fluid plug 10-1 may have a fluid portion 10-1B removed from it, which mixes with the third fluid 10-3A in the third fluid plug 10-3. As the fluids continue to flow in the channel segment, the third fluid plug 10-3 may have a fluid portion 10-3D (i.e., a mixture of the first and third fluids) removed from it that mixes with the fluid in the fifth fluid plug 10-5. The fifth fluid plug 10-5 may subsequently have a fluid portion 10-5D removed from it that contains a mixture of the first, third, and fifth fluids. This fluid portion may mix with seventh fluid plug 10-7.

In some embodiments, the mixing and process of removal of a fluid from a fluid plug may continue until each fluid plug contains fluid from at least a portion of the miscible fluids upstream. However, in other embodiments, only fluids from certain fluid plugs are mixed with one another, while fluids from other fluids plugs are not mixed. The amount of mixing and the number of fluids plugs that are mixed together may be controlled, for example, by determining the length of intervening fluids between fluid plugs, the volume of the fluid plugs, the phase of the fluid plugs, the viscosity of the fluid plugs, the flow speed of the fluid plugs, the surface tension of the fluids, the polarity of the fluids, the density of the fluids, the interfacial surface tension between adjacent fluids, interfacial surface tension between the fluid plug and the channel wall, channel design (e.g., geometry, length, radius of curvature of corners), and properties of the channel wall (e.g., surface roughness, surface texture, surface energy). Other factors may also contribute to the amount of mixing.

It should also be appreciated that while removal of a fluid portion from a fluid plug may result in that fluid portion being added to another fluid plug (which results in mixing) in some embodiments, in other embodiments, the fluid portion is not added to another fluid plug and does not result in mixing between fluid plugs. The fluid plug may be used for a different purpose, such as for priming the walls of the channel segment (e.g., to change the surface tension of the channel wall) or for other purposes. For example, in some embodiments, as a fluid plug (e.g., first fluid plug 10-1 of FIG. 3A) flows in the channel segment, fluid portion 10-1B is removed from the fluid plug but continues to travel down the channel segment from a downstream side to an upstream side. The fluid may be designed to not substantially mix with any subsequent fluid in the channel segment and may end up in the waste region without being substantially combined into a fluid plug. Other configurations of fluid flow are also possible.

In some embodiments, the amount of mixing and/or the number of fluids plugs that are mixed together may be controlled by certain characteristics of the fluid plugs. In some embodiments, the amount and/or duration of mixing may be controlled in part by the distance between fluid plugs or the length/volume of the intervening fluids in a channel segment. For example, if it is desirable to have two fluids mix, they may be positioned relatively close to one another in a channel segment (e.g., first and third fluids in FIG. 1A). If it is undesirable to have two fluids mix, they may be positioned relatively farther away from one another in a channel segment (e.g., first and eleventh fluids in FIG. 1A). In certain embodiments, a longer (more voluminous) intervening fluid plug will separate fluid plugs to a greater extent than a shorter (less voluminous) intervening fluid plug, and may prevent two fluid plugs from mixing due to their long separation in the channel segment. In some instances, a larger percentage of volume reduction of a fluid plug, for a given channel length and flow time, may be achieved with a shorter (less voluminous) fluid plug compared to a longer (more voluminous) fluid plug.

The phase of the fluid plugs may be used, in some instances, to prevent mixing. For instance, a fluid plug in the liquid phase and its liquid fluid portion may not be able to mix with fluid plugs in the gas phase. Accordingly, where it is desirable to have fluids mix, such fluids may be miscible with one another to facilitate mixing in some embodiments. Where it is undesirable to have fluids mix, they may be designed to be immiscible with one another in certain embodiments.

In some cases, the viscosity of the fluid plug may influence mixing within the fluid plug. For example, a more viscous fluid plug may have reduced mixing through various mechanisms, such as circulating currents and diffusion, compared to a less viscous fluid plug. A relatively more viscous fluid may also deposit less fluid on the walls of a channel segment during fluid flow compared to a relatively less viscous fluid in some embodiments.

The flow speed of the fluid plugs may also influence mixing within a fluid plug and the removal of a fluid portion from the fluid plug (e.g., deposition of the fluid portion on a wall of the channel segment). For instance, faster flow speeds may result in larger amounts of fluid being removed from a fluid plug, for a given amount of flow time, compared to removal at slower flow speeds. In some embodiments, slower flow speeds may result in enhanced diffusion of a fluid portion into a fluid plug compared to flow at higher flow speeds.

In some instances, mixing may be controlled using more than one characteristic, such as more than one of the characteristics described above (e.g., volume and phase of the fluids). Other methods of controlling mixing based on characteristics of the fluid plugs are also possible. In certain embodiments, the amount of mixing and/or the number of fluids plugs that are mixed together may be controlled by certain properties of the fluids. For instance, a fluid or fluid plug that has a lower surface tension with respect to a channel wall may more readily facilitate removal of a fluid portion from the fluid plug (e.g., produce a fluid portion that is deposited on the channel wall) than a fluid/fluid plug that has a higher surface tension with respect to the channel wall. Thus, the relative surface tension of the fluid can be varied to control the amount of fluid removed from a fluid plug (and, therefore, the subsequent amount of mixing between fluids).

In certain embodiments, the surface tension between a fluid and a channel wall may be selected as desired. In some cases, a wetting agent may be added to a fluid or fluid plug to control the surface tension. The wetting agent may be added, for example, prior to mixing, as a result of mixing, or as a result of a fluid being removed from a fluid plug. In certain cases, a wetting agent may be added to the channel wall to control surface tension, e.g., during manufacturing of the device, prior to fluid flow, and/or as a result of fluid flow. In general, any suitable wetting agent at any desired concentration may be used. Examples of suitable wetting agents include, but are not limited to, polyvinyl alcohol, non-ionic detergents (e.g., poly(ethylene oxide) derivatives like Tween 20 and Triton, fatty alcohols), anionic detergents (e.g., sodium dodecyl sulfate and related detergents with shorter or longer alkane chains such as sodium decyl sulfate or sodium octadecyl sulfate, or fatty acid salts), cationic detergents (e.g., quaternary ammonium cations such as cetyl trimethylammonium bromide), zwitterionic detergents (e.g., dodecyl betaine), perfluorodetergents (e.g., Capstone FS-10), low surface tension liquids (e.g., alcohols such as isopropanol), and combinations thereof. In certain embodiments, a non-wetting agent (e.g., ionic compounds) may be added to increase the surface tension.

In embodiments in which a wetting agent is added to a fluid or fluid plug, the percentage (by weight/volume) of the wetting agent in the fluid or fluid plug may be greater than or equal to about 0.001%, greater than or equal to about 0.01%, greater than or equal to about 0.025%, greater than or equal to about 0.05%, greater than or equal to about 0.1%, greater than or equal to about 0.1%, greater than or equal to about 0.5%, greater than or equal to about 1%, greater than or equal to about 5%, greater than or equal to about 10%, greater than or equal to about 20%, greater than or equal to about 30%, greater than or equal to about 40%, or greater than or equal to about 40%. In some instances, the percentage of wetting agent in the fluid or fluid plug may be less than or equal to about 75%, less than or equal to about 50%, less than or equal to about 40%, less than or equal to about 30%, less than or equal to about 20%, less than or equal to about 10%, less than or equal to about 5%, less than or equal to about 1%, less than or equal to about 0.5%, less than or equal to about 0.01%, or less than or equal to about 0.01%. Combinations of the above-referenced ranges are also possible (e.g., greater than or equal to about 0.01% or less than or equal to about 50%). Other ranges of wetting agent percentages are also possible.

Polarity of the fluids may also influence mixing. For example, in some embodiments fluids with differing polarities (e.g., a water based fluid and an oil based fluid) may not mix or may mix to a relatively lesser extent, while fluids with similar polarities (e.g., a water based fluid and a methanol based fluid) may mix or may mix to a relatively greater extent. In some cases, polarity may be used to prevent or limit adjacent fluids from mixing and/or prevent or limit fluid portions from mixing with certain non-adjacent fluid plugs. In other cases, polarity may be used to prevent or limit adjacent fluids from mixing and allow fluid portions to mix with certain non-adjacent fluid plugs.

In some instances, the density of the fluids may be used to control mixing. Significant differences in density between fluids may prevent or limit the fluids from mixing. Conversely, fluids with similar densities may readily mix.

In certain cases, the interfacial tension between fluids may also influence mixing. For instance, fluids with a high interfacial tension with each other may not mix or may mix to a lesser extent, while fluids with a low interfacial tension with one another may mix to a relatively greater extent. In some cases, interfacial tension may be used to prevent or limit adjacent fluids from mixing and prevent or limit fluid portions from mixing with certain non-adjacent fluid plugs. In other cases, interfacial tension may be used to prevent or limit adjacent fluids from mixing and allow fluid portions to mix with certain non-adjacent fluid plugs.

In some instances, mixing may be controlled using more than one property described herein (e.g., surface tension and polarity). Other methods of controlling mixing based on properties of the fluids are also possible.

In some embodiments, the amount of mixing and/or the number of fluids plugs that are mixed together may be controlled by certain characteristics of the channel segment. For instance, the geometry of the channel segment may be used to control mixing. Non-limiting examples of geometrical channel features that may influence mixing include cross-sectional shape, cross-sectional area, aspect ratio, hydraulic diameter, radius of curvature of internal corners, deviations in the channel (e.g., turns, bends), radius of curvature of deviations in the channel, and gradual and/or abrupt changes in channel geometry (e.g., changes in cross-section area). For instance, a channel cross-section with sharper corners may more readily facilitate removal of a fluid from a fluid plug compared to a channel cross-section with blunt corners. In one example, a channel with a cross-section that includes a radius of curvature substantially smaller than the half-width and/or half-height of the channel may more readily facilitate removal of a fluid from a fluid plug compared to a channel cross-section that does not include such a radius of curvature, or a channel cross-section having a relatively larger radius of curvature. A radius of curvature substantially smaller than the half-width and/or half-height of the channel may be, for example, less than or equal to about 50%, less than or equal to about 40%, less than or equal to about 30%, less than or equal to about 20%, less than or equal to about 10%, or less than or equal to about 5% of the half-width and/or half-height of the channel. Additional examples of channel configurations and dimensions are provided in more detail below.

The length of the channel segment may also be used to control mixing. For example, longer channel segments may allow greater volume reduction of a fluid plug compared to a shorter channel, with all other factors being equal. In some cases, a channel that is substantially longer than the length occupied by the fluid plug may allow greater volume reduction of the fluid (e.g., the entire volume) than a channel that is not substantially longer than the length occupied by the fluid plug. Examples of values of lengths are provided in more detail below. In some instances, mixing may be controlled using more than one characteristic (e.g., cross-section shape and length). Other methods of controlling mixing based on characteristics of the channel are also possible.

In some embodiments, the amount of mixing and/or the number of fluids plugs that are mixed together may be controlled by certain characteristics of a channel wall (e.g., surface roughness, surface texture, surface energy, surface polarity, surface charge, interfacial surface tension between the channel wall and a fluid, local variations in the characteristics of the channel wall). For instance, the surface roughness of a channel wall may be selected to facilitate or prevent removal of a fluid portion from a fluid plug. A channel wall with a higher surface roughness may more readily facilitate removal of a fluid portion from a fluid plug than a channel wall with a lower surface roughness.

In some embodiments, a channel segment (or a portion thereof) may have a root mean square surface (RMS) roughness of less than about less than or equal to about 10 microns. In certain embodiments, the RMS surface roughness may be, for example, less than or equal to about 5 microns, less than or equal to about 3 microns, less than or equal to about 1 micron, less than or equal to about 0.8 microns, less than or equal to about 0.5 microns, less than or equal to about 0.3 microns, less than or equal to about 0.1 microns, less than or equal to about 0.08 microns, less than or equal to about 0.05 microns, less than or equal to about 0.08 microns, less than or equal to about 0.01 microns, or less than or equal to about 0.005 microns. In some instances, the RMS surface roughness may be greater than or equal to about 0.005 microns, greater than or equal to about 0.01 microns, greater than or equal to about 0.05 microns, greater than or equal to about 0.1 microns, greater than or equal to about 0.5 microns, greater than or equal to about 1 micron, or greater than or equal to about 3 microns. Combinations of the above-referenced ranges are also possible (e.g., greater than or equal to about 0.05 microns and less than or equal to about 5 microns. RMS surface roughness is a tem known to those skilled in the art, and may be expressed as:

$$\sigma_h = [\langle (z-z_m)^2 \rangle]^{1/2} = \left[ \frac{1}{A} \int_A (z-z_m)^2 \, dA \right]^{1/2}$$

where A is the surface to be examined, and $|z-z_m|$ is the local height deviation from the mean.

In general, surface roughness and/or surface texture of the channel may be formed during fabrication or later modified using any suitable method. Exemplary methods of fabricating or modifying the surface roughness and/or surface texture of the channel include chemical etching (e.g., acid, alkaline, corrosive solvent), plasma etching (e.g., low pressure, atmospheric, flame, plasma etching with inert and/or reactive gases), electrochemical etching, corona discharge, mechanical methods (e.g., mechanical machining, laser machining, mechanical polishing, mechanical grinding, bead-blasting, grit-blasting, shot-peening), ultrasonic machining, electrical methods (e.g., electrochemical polishing, electric discharge machining, electroforming), coating (e.g., by spray-coating, physical vapor deposition, chemical vapor deposition, painting), and combinations thereof. In some instances, the surface roughness and/or texture may be produced using a molding process. The surface texture and/or roughness of the mold may be modified using any of the above methods and/or coating or plating the mold surface. Other methods of producing a desired surface texture and/or surface roughness are also possible.

In some instances, the surface charge of a channel wall may be used to control mixing. In one example, the surface charge of a channel wall may be used to facilitate the formation of a fluid portion of an oppositely charged fluid. In some embodiments, the surface charge density on a channel wall or a portion thereof may be greater than or equal to about $0 \text{ C/m}^2$, greater than or equal to about $0.01 \text{ C/m}^2$, greater than or equal to about $0.05 \text{ C/m}^2$, greater than or equal to about $0.1 \text{ C/m}^2$, or greater than or equal to about $0.5 \text{ C/m}^2$. In some instances, the surface charge density on a channel wall or portion thereof may be less than or equal to about $1 \text{ C/m}^2$, less than or equal to about $0.5 \text{ C/m}^2$, less than or equal to about $0.1 \text{ C/m}^2$, or less than or equal to about $0.05 \text{ C/m}^2$. Combinations of the above-referenced ranges are also possible (e.g., greater than or equal to about $0 \text{ C/m}^2$ and less than or equal to about $1 \text{ C/m}^2$). Other values of surface charge density are also possible.

In some instances, mixing may be controlled using more than one characteristic (e.g., surface energy, surface polarity, and surface roughness). Other methods of controlling mixing based on characteristics of a channel wall are also possible. It should also be understood that other characteristics of a channel wall can be used to control mixing.

In some embodiments, the surface energy of a channel wall or a portion thereof may be used to control mixing. In some instances, the surface energy of a channel wall may be greater than or equal to about 10 dynes/cm, greater than or equal to about 25 dynes/cm, greater than or equal to about 50 dynes/cm, greater than or equal to about 75 dynes/cm, greater than or equal to about 100 dynes/cm, greater than or equal to about 200 dynes/cm, greater than or equal to about 300 dynes/cm, or greater than or equal to about 400 dynes/cm. In some embodiments, the surface energy of a channel wall may be less than or equal to about 500 dynes/cm, less than or equal to about 400 dynes/cm, less than or equal to about 300 dynes/cm, less than or equal to about 200 dynes/cm, less than or equal to about 100 dynes/cm, less than or equal to about 75 dynes/cm, or less than or equal to about 25 dynes/cm. Combinations of the above-referenced ranges are also possible (e.g., greater than or equal to about 10 dynes/cm and less than or equal to about 200 dynes/cm). Other values of surface energy are also possible.

As known to those of ordinary skill in the art, surface energy includes both a polar component and a dispersion (non-polar) component. In some embodiments, the surface polarity (e.g., as indicated by the ratio of the polar component to the dispersive component of the surface energy) of a channel wall or a portion thereof may be used to control mixing. For example, for a cyclo-olefin copolymer the surface polarity is 0 (entirely dispersive), for water the surface polarity is 2.3 (fairly polar), and for plasma-treated surfaces the surface polarity may have a ratio of 3 or more.

In some instances, the ratio of the polar component to the dispersive component of the surface energy may be greater than or equal to about 0, greater than or equal to about 0.5, greater than or equal to about 1, greater than or equal to about 1.5, greater than or equal to about 2 greater than or equal to about 2.5, greater than or equal to about 3, greater than or equal to about 3.5, or greater than or equal to about 4. In some embodiments, the ratio of the polar component to the dispersive component of the surface energy may be less than or equal to about 5, less than or equal to about 4.5, less than or equal to about 4, less than or equal to about 3.5, less than or equal to about 3, less than or equal to about 2.5, less than or equal to about 2, less than or equal to about 1.5, or less than or equal to about 1. Combinations of the above-referenced ranges are also possible (e.g., greater than or equal to about 0 and less than or equal to about 3). Other values of surface polarity are also possible.

In some embodiments, the surface charge, surface energy, and/or surface polarity of the channel may be selected as desired. In general, surface charge, surface energy, and/or surface polarity of the channel may be formed during fabrication or later modified using any suitable method. Exemplary methods of fabricating or modifying the surface charge, surface energy, and/or surface polarity of the channel include exposure to reactive agents (e.g., redox agents, permanganate, peroxides, chromic acid, other acids, alkaline solutions, corrosive solvent), plasma exposure (e.g., low pressure, atmospheric, flame, plasma etching with inert and/or reactive gases), surface functionalization, coating methods (e.g., evaporation, sputtering, vapor deposition processes, electroless plating, chemical deposition processes, electrochemical deposition processes), and combinations thereof. In some instances, a portion of the channel may be coated with materials such as metallic material, non-metallic material, nanoparticles, surface reactive agents, amine reactive group (e.g., NHS-activated molecules, molecules with carboxylic acid or aldehyde), thiol-reactive groups (e.g., maleimido-activated molecules), carboxy-reactive groups (e.g., amines), polyelectrolyte (e.g., polyethylene amine, dextran sulfate, copolymer with charged side chains), hydrophobic or partially hydrophobic material (e.g., co-polymer with hydrophobic chains such as polystyrene), silane (e.g., methoxysilanes, ethoxysilanes, trichloro(1H,1H,2H,2H-perfluorooctyl)silane, epoxy silanes), parylene, silicon dioxide, polyvinyl pyrrolidone, carbon-based nanostructures (e.g., carbon nanotubes), photosensitive molecules (e.g., derivatives of diazirine), biomolecules (e.g., proteins, DNA, carbohydrates, lipids, amino acid side chains), and combinations thereof. Other methods of producing a desired surface charge, surface energy, and/or surface polarity on channel are also possible.

In certain cases, as shown in illustratively FIG. 3D the entire volume of a fluid (e.g., the first fluid) may be incorporated into one or more fluid plugs downstream such that the fluid plug is no longer present in the channel segment. In some cases, the volume of the fluid in the fluid plug may be reduced by a certain percentage (e.g., compared to the initial volume of the fluid plug). For instance, in some embodiments, the volume of a fluid plug may be reduced by greater than or equal to about 50%, greater than or equal to about 60%, greater than or equal to about 70%, greater than or equal to about 80%, greater than or equal to about 90%, or greater than or equal to about 95%. In some instances, the volume of a fluid in a fluid plug may be reduced by less than or equal to about 100%, less than or equal to about 90%, less than or equal to about 80%, less than or equal to about 70%, or less than or equal to about 60%. Combinations of the above-referenced ranges are also possible (e.g., greater than or equal to about 50% and less than or equal to about 100%). In some cases, 100% of the volume of the fluid is removed from a fluid plug, such that the fluid plug no longer remains in the system. In such embodiments, the fluid removed from the fluid plug may be entirely dispersed along or within the channel. In other embodiments, 0% of the fluid is removed from a fluid plug during fluid flow. Other values of volume reduction percentage are also possible. As described herein, in some embodiments the volume of more than one fluid plugs is reduced by the amounts noted above.

In addition to fluid plugs, a channel segment may also contain at least one substantially dry reagent in some embodiments (e.g., during storage and/or prior to a flowing step described herein). An example of mixing between a fluid from a fluid plug and a substantially dry reagent is shown in FIGS. 4A-E. As shown illustratively in FIG. 4A, a channel segment 5, including an upstream portion 7 and a downstream portion 8, may contain a substantially dry reagent 30, first fluid plug 10-1, a second fluid plug 20-2, a third fluid plug 10-3. The fluid plugs may contain a first fluid 10-1A, a second fluid 20-2A, and a third fluid 10-3A, respectively. As shown illustratively in this figure, the second fluid plug may be positioned between the first and third fluid plugs. In some cases, the second fluid may be immiscible with the first and third fluids, while the first and third fluids may optionally be miscible with one another. Additionally, as shown in the figure, the substantially dry reagent may be positioned downstream of the fluid plugs. In general, however, the substantially dry reagent may have any suitable position relative to the fluid plugs. For instance, the substantially dry reagent may be positioned between two fluid plugs in some embodiments. In some cases, a substantially dry reagent is positioned in a gaseous fluid plug (e.g., air) which is flanked on both ends by two liquid fluid plugs. Such a configuration may be appropriate for storage of the reagents in certain embodiments.

As shown in FIG. 4B, the fluids may be flowed in series toward the substantially dry reagent, e.g., from upstream to downstream in the direction of arrow 9. In some embodiments, flowing first fluid plug 10-1 over the substantially dry reagent may cause the first fluid to mix with the reagent (which is no longer substantially dry). The reagent may mix with the first fluid to form a homogenous or heterogeneous (e.g., solution or suspension) mixture. During flow, a mixture 10-1C of the first fluid and reagent may leave a fluid portion 10-1D, which may be immiscible with second fluid 20-2A and miscible with third fluid 10-3A, as illustrated in FIG. 3C. As shown in FIGS. 3D-E, fluid portion 10-1D may mix with the third fluid in the third fluid plug to form a mixture of the first fluid, the reagent, and third fluid 10-3E. In certain cases, the entire volume of the mixture of the first fluid and the reagent may be removed from first fluid plug 10-1 and may mix with the third fluid plug.

Fluids can be flowed in a device described herein using any suitable method. In some embodiments, a fluidic device employs one or more vent valves to controllably flow and/or mix portions of fluid within the system. The vent valves can comprise, for example, a port in fluid communication with the channel in which a fluid is positioned, and may be actuated by positioning a seal over the port opening or by removing the seal from the port opening. In certain embodiments, the seal may include a valving mechanism such as a mechanical valve operatively associated with a tube in fluid communication with the port. Generally, opening the vent valve allows the port to function as a vent. When the port functions as a vent, the fluid located on one side of the vent valve flows, while the fluid located on the opposite side of the vent valve relative to the first fluid remains stationary. When the valve is closed, the port no longer functions as a vent, and the fluid located on both sides of the vent valve can flow through the system towards an outlet. Advantageously, fluid control such as a sequence of fluid flow and/or a change in flow rate, can be achieved by opening and closing one or more vent valves and by applying a single source of fluid flow (e.g., a vacuum) operated at a substantially constant pressure. This can simplify the operation and use of the device by an intended user. Vent valves are described in more detail in U.S. Patent Publication No. 2011/0120562, filed Nov. 24, 2010 and entitled "Fluid Mixing and Delivery in Microfluidic Systems," which is incorporated herein by reference in its entirety for all purposes.

In some embodiments, when the fluid flow source is activated, one or more channels in the fluidic device may be pressurized (e.g., to approximately −30 kPa) which may drive the fluids within the channel toward the outlet. In some embodiments, fluids can be stored serially in a channel upstream of a vent valve positioned along the channel, and after closing the vent valve, the fluids can flow sequentially towards the channel outlet. In some cases, fluids can be stored in separate, intersecting channels, and after closing a vent valve the fluids can be flowed sequentially. The timing of delivery and the volume of fluid can be controlled, for example, by the timing of the vent valve actuation.

Figure 6B:
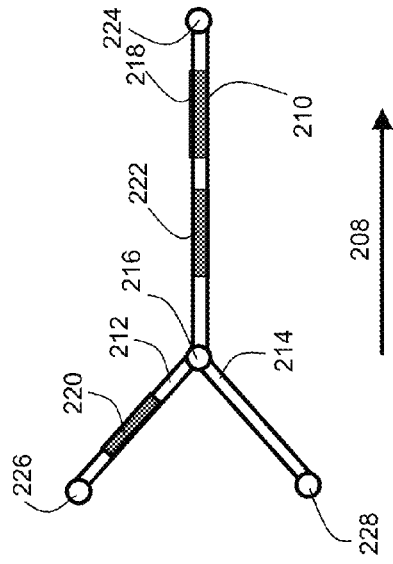
FIGS. 6A-6C show methods of mixing involving the use of vent valves according to one set of embodiments.
Figure 6A:
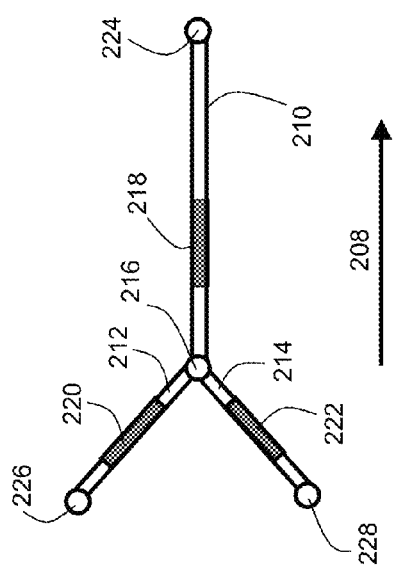
Figure 6C:
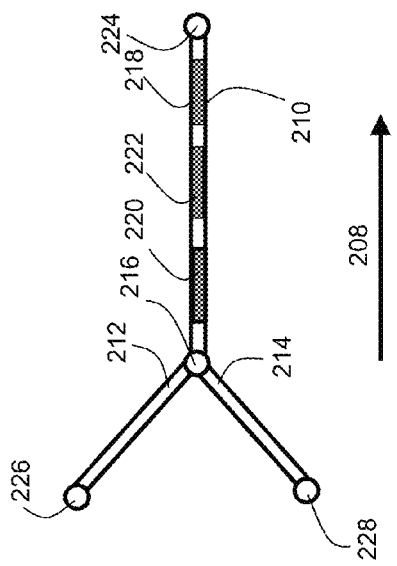
Figure 7:
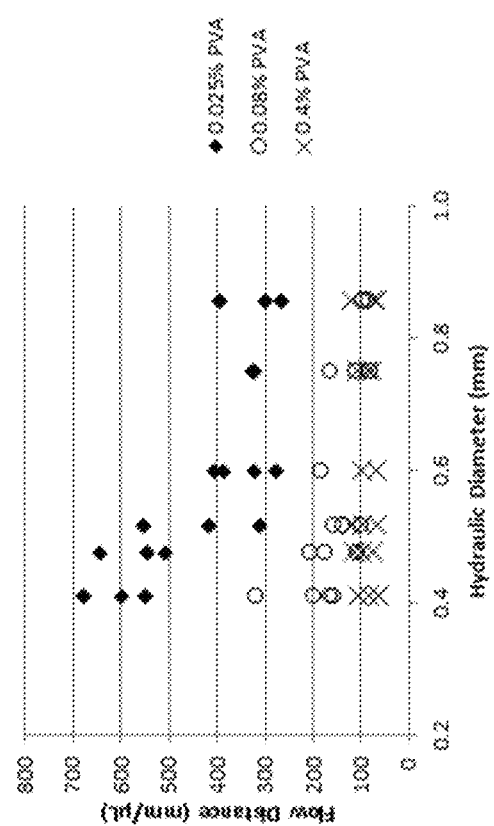
FIG. 7 shows a plot demonstrating the influence of hydraulic channel diameter on mixing according to one set of embodiments.

An example of controlling movement of fluid plugs in a fluidic device comprising multiple channel segments (e.g., branching channels) and at least one vent valve is shown in FIGS. 6A-6C. In the device illustrated in FIG. 6A, a channel segment 210 is fluidically connected to two channel segments (e.g., branching channels) 212 and 214, which intersected at vent valve 216. As shown in this figure, channel segment 210 may optionally contain fluid plug 218. In some embodiments, fluids plugs 220 and 222 may be stored and/or sealed in channel segments 212 and 214, respectively (e.g., prior to first use of the device). Channel segment 210 is shown connected to outlet 224, while channel segments 212 and 214 are shown connected to inlets 226 and 228, respectively. All of the fluids in the device may be separated by plugs of gas (immiscible with fluid plugs 218, 220 and 222).

As shown illustratively in FIG. 6B, fluids 220 and 222 may be transported sequentially. To transport fluid plug 222, vent valve 216 and inlet 228 may be both closed (while inlet 226 is opened). To transport fluid plug 220 after fluid plug 222 is transported, vent valve 216 and inlet 226 may be both closed (while inlet 228 is opened). Mixing can then occur between fluid plugs 218, 222 and/or 220 in channel segment 210 as described herein (e.g., with respect to FIGS. 1-4). The timing of when the vent valves are opened or closed can be used to vary the length/volume of the plugs of gas separating fluid plugs 218, 222 and/or 220, as well as the duration of fluid flow.

Advantageously, vent valves can be operated without constricting the cross-section of the microfluidic channel on which they operate, as might occur with certain valves in the prior art. Such a mode of operation can be effective in preventing leaking across the valve. Moreover, because vent valves can be used, some systems and methods described herein do not require the use of certain internal valves, which can be problematic due to, for example, their high expense, complexity in fabrication, fragility, limited compatibility with mixed gas and liquid systems, and/or unreliability in microfluidic systems.

It should be understood that while vent valves are described, other types of valving mechanisms can be used with the systems and methods described herein. Non-limiting examples of a valving mechanism which may be operatively associated with a valve include a diaphragm valve, ball valve, gate valve, butterfly valve, globe valve, needle valve, pinch valve, poppet valve, or pinch valve. The valving mechanism may be actuated by any suitable means, including a solenoid, a motor, by hand, by electronic actuation, or by hydraulic/pneumatic pressure.

As described herein, in some embodiments, reagents (e.g., for a chemical and/or biological reaction) may be stored in fluid and/or dry form in a fluidic device. The method of storage may depend on the particular application. Reagents can be stored, for example, as a liquid, a gas, a gel, a plurality of particles, or a film. The reagents may be positioned in any suitable portion of a device, including, but not limited to, in a channel or channel segment, reservoir, on a surface, and in or on a membrane, which may be part of a reagent storage area. A reagent may be associated with a fluidic system (or components of a system) in any suitable manner. For example, reagents may be crosslinked (e.g., covalently or ionically), absorbed, or adsorbed (physisorbed) onto a surface within the fluidic system. In some cases, a liquid is contained within a channel or reservoir of a device.

In certain embodiments, one or more channel segments of a fluidic device includes a stored liquid reagent (e.g., in the form of a fluid plug). In some cases, more than one liquid reagents (e.g., fluid plugs) are stored in a channel or channel segment. The liquid reagents may be separated by a separation fluid, which may be immiscible with the liquid reagents. The fluid reagents may be stored in the device prior to first use, or introduced into the device at first use. In some cases, the liquid reagents may be kept separate during storage of the fluids (e.g., while the device is sealed). During use of the device, at least portions of the liquids may be combined (e.g., mixed) using the methods described herein.

Certain fluidic devices may be designed to include both liquid and dry reagents stored in a single article prior to first use and/or prior to introduction of a sample into the device. In some cases, the liquid and dry reagents are stored in fluid communication with each other prior to first use. In other cases, the liquid and dry reagents are not in fluid communication with one another prior to first use, but at first use are placed in fluid communication with one another. For instance, one or more liquid reagents may be stored in a first common channel and one or more dry reagents stored in a second common channel, the first and second common channels not being connected or in fluidic communication with one another prior to first use. Additionally or alternatively, the reagents may be stored in separate vessels such that a reagent is not in fluid communication with the fluidic device prior to first use. The use of stored reagents can simplify use of the fluidic device by a user, since this minimizes the number of steps the user has to perform in order to operate the device. This simplicity can allow the fluidic devices described herein to be used by untrained users, such as those in point-of-care settings, and in particular, for devices designed to perform immunoassays.

In various embodiments involving the storage of fluid (e.g., liquid) reagents prior to first use, the fluids may be stored (and, in some embodiments, statically maintained without mixing) in a fluidic device for greater than 10 seconds, one minute, one hour, one day, one week, one month, or one year. By preventing contact between certain fluids, fluids containing components that would typically react or bind with each other can be prevented from doing so, e.g., while being maintained in a common channel. For example, while they are stored, fluids (e.g., in the form of fluid plugs) may be kept separated at least in part by immiscible separation fluids so that fluids that would normally react with each other when in contact may be stored for extended periods of time in a common channel. In some embodiments, the fluids may be stored so that they are statically maintained and do not move in relation to their position in the channel. Even though fluids may shift slightly or vibrate and expand and contract while being statically maintained, certain fluidic devices described herein are adapted and arranged such that fluids in a common channel do not mix with one another during these processes.

Fluidic devices that are used for storage of one or more reagents (e.g., prior to first use) may be stored at reduced temperatures, such as less than or equal to 10° C., 4° C., 0° C., or −10° C. Fluids may also be exposed to elevated temperatures such as greater than 25° C., greater than 35° C. or greater than 50° C. Fluids may be shipped from one location to the other by surface or air without allowing for mixing of reagent fluids contained in the channel. The amount of separation fluid may be chosen based on the end process with which the fluids are to be used as well as on the conditions to which it is expected that the fluidic device will be exposed. For example, if the fluidic device is expected to receive physical shock or vibration, fluids may only fill portions but not all of a channel segment. Furthermore, larger plugs of immiscible separation fluid may be used along with one or more channel configurations described herein. In this manner, distinct fluids within a channel system of a fluidic device may avoid mixing.

A fluidic device may include one or more characteristics that facilitate control over fluid transport and/or prevent fluids from mixing with one another during storage. For example, a device may include structural characteristics (e.g., an elongated indentation or protrusion) and/or physical or chemical characteristics (e.g., hydrophobicity vs. hydrophilicity) or other characteristics that can exert a force (e.g., a containing force) on a fluid. In some cases, a fluid may be held within a channel using surface tension (e.g., a concave or convex meniscus). For example, certain portions of a channel segment may be patterned with hydrophobic and hydrophilic portions to prevent movement and/or mixing of fluids during storage. One measure of hydrophobicity that can be useful in selecting such materials is contact angle measurements taken between water and a candidate material. While "hydrophobic" can be considered a relative term in some cases, a particular degree or amount of hydrophobicity can be easily selected by those of ordinary skill in the art, with the aid of knowledge of the characteristics of particular materials and/or readily-determined contact angle measurements for selecting fluids and/or materials described herein.

In some cases, a channel may segment have an absence of inner walls or other dividers to keep the fluids apart and fluids may be separated by a separation fluid as described herein.

In some embodiments, fluids can be stored on two sides of a fluidic device, as described in more detail in U.S. Patent Publication No. 2010/0158756, filed Dec. 17, 2009, entitled "Reagent Storage in Microfluidic Systems and Related Articles and Methods," which is incorporated herein by reference in its entirety for all purposes. In some cases, the fluidic device may include channel segments having non-circular cross sections and channel segments having circular cross-sections. In certain embodiments, at least some of the channel segments having circular cross-sections may pass through the thickness of the article and may connect channels formed on either surfaces of the article.

In some embodiments, a channel segment may include one or more corners (e.g., curved corners) having a certain radius of curvature. The curved corner may be, for example, a convex portion of a surface that mates with a cover. The convex portion of the surface may be formed during fabrication of the channel segment by various techniques (e.g., injection molding). In certain embodiments, a channel segment may include one or more corners (e.g., curved corners) having a radius of curvature of, for example, less than or equal to about 100 µm, less than or equal to about 50 µm, less than or equal to about 30 µm, less than or equal to about 20 µm, less than or equal to about 10 µm, less than or equal to about 5 µm, less than or equal to about 3 µm, less than or equal to about 2 µm, less than or equal to about 1 µm, less than or equal to about 0.5 µm, or less than or equal to about 0.1 µm. In some embodiments, the radius of curvature of a curved corner of a channel may be, e.g., greater than or equal to about 0.1 µm, greater than or equal to about 0.5 µm, greater than or equal to about 1 µm, greater than or equal to about 2 µm, greater than or equal to about 3 µm, greater than or equal to about 5 µm, greater than or equal to about 10 µm, greater than or equal to about 20 µm, greater than or equal to about 30 µm, greater than or equal to about 50 µm, or greater than or equal to about 100 µm. Combinations of the above-noted ranges are also possible (e.g., a radius of curvature of greater than or equal to about 1 micron and less than or equal to about 20 microns). Other ranges are also possible. A curved corner having a relatively smaller radius of curvature may increase the amount of fluid being removed from a fluid plug flowing along a portion of the channel, compared to a fluid plug flowing in a channel having a relatively larger radius of curvature.

In some embodiments, a channel having a curved corner may have a ratio of a cross-sectional dimension (e.g., a width or a height) of the channel to the radius of curvature of the substantially curved corner of greater than or equal to about 1:1, greater than or equal to about 2:1, greater than or equal to about 3:1, greater than or equal to about 5:1, greater than or equal to about 10:1, greater than or equal to about 20:1, greater than or equal to about 30:1, greater than or equal to about 50:1, greater than or equal to about 100:1, greater than or equal to about 200:1, or greater than or equal to about 500:1. In some instances, the ratio of a cross-sectional dimension (e.g., a width or a height) of the channel to the radius of curvature of the substantially curved corner may be less than or equal to about 600:1, less than or equal to about 400:1, less than or equal to about 200:1, less than or equal to about 100:1, less than or equal to about 75:1, less than or equal to about 50:1, less than or equal to about 25:1, less than or equal to about 10:1, or less than or equal to about 5:1. Combinations of the above-referenced ranges are also possible (e.g., greater than or equal to about 5:1 and less than or equal to about 400:1). Other values of the ratio of a cross-sectional dimension (e.g., a width or a height) of the channel to the radius of curvature of the substantially curved corner are also possible.

In some fluidic devices described herein, it is desirable to have fluidic components (e.g., channel, channel segment, channel portion) having non-zero draft angles. As known to those of ordinary skill in the art, a draft angle is the amount of taper, e.g., for molded or cast parts, perpendicular to the parting line. For example, as shown illustratively in FIG. 5A, a substantially rectangular channel 125, which has walls 125-A and 125-C that are substantially perpendicular to surface 121 (e.g., a parting line), has a draft angle 196 of 0°. The cross sections of fluidic channels having non-zero draft angles, on the other hand, may resemble a trapezoid, a parallelogram, or a triangle. For example, as shown in the embodiment illustrated in FIG. 5B, channel 127 has a substantially trapezoidal cross-section. Draft angle 196 is formed by the angle between a line perpendicular to surface 121 and wall 127-A of the channel, and is non-zero in this embodiment.

Figure 12A:
FIGS. 12A-12C show channels including different draft angles according to one set of embodiments.
Figure 12B:
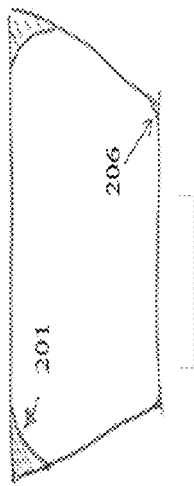
Figure 12C:
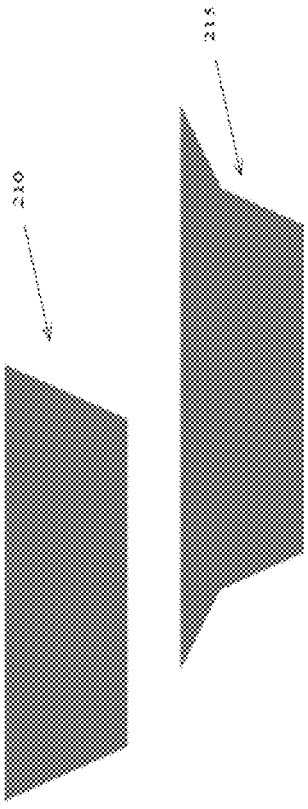

In some embodiments, during fluid flow a corner of a channel having a draft angle less than 90° may cause a fluid to deposit a relatively larger fluid portion than a corner of a channel having a draft angle greater than or equal to 90°, as shown in FIG. 12. FIG. 12A shows a cross-section of a channel portion including corners a draft angle 200 less than 90° and a draft angle 205 greater than 90°. During fluid flow, a fluid portion 201 in the corner of the channel encompassing draft angle 200 may be greater than a fluid portion 206 in the corner encompassing draft angle 205, as shown illustratively in FIG. 12B. In certain embodiments, the amount of a fluid portion deposited in a corner of a channel may increase with decreasing draft angle. For example, more fluid may be deposited in channel portion 215 than channel portion 210 shown in FIG. 12C.

The draft angle of a channel, channel segment, or channel portion, for example, greater than or equal to about to about 1°, greater than or equal to about 2°, greater than or equal to about 3°, greater than or equal to about 5°, greater than or equal to about 8°, greater than or equal to about 10°, greater than or equal to about 20°, greater than or equal to about 30°, greater than or equal to about 45°, greater than or equal to about 60°, or greater than or equal to about 75°. In some instances, the draft angle may be less than or equal to about 90°, less than or equal to about 75°, less than or equal to about 60°, less than or equal to about 45, less than or equal to about 30°, less than or equal to about 20°, less than or equal to about 10°, or less than or equal to about 5°. Combinations of the above-referenced ranges are also possible (e.g., greater than or equal to about 1° and less than or equal to about 60°).

It should be understood that a channel, channel segment, or channel portion can have any suitable cross-sectional dimension, which may depend on, for example, where the channel is positioned, how the channel is to be used (e.g., for mixing or for storage of reagents), the size of the fluidic device, the volume of reagents intended to flow in the device, etc. For instance, in some embodiments, a channel, channel segment, channel portion, etc. may have a maximum cross-sectional dimension (e.g., a width or height) of less than or equal to about 5 mm, less than or equal to about 3 mm, less than or equal to about 1 mm, less than or equal to about 750 microns, less than or equal to about 600 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, or less than or equal to about 5 microns. In some instances, a channel, channel segment, or channel portion, may have a maximum cross-sectional dimension of greater than or equal to about 0.1 microns, greater than or equal to about 1 microns, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 400 microns, greater than or equal to about 600 microns, greater than or equal to about 900 microns, greater than or equal to about 1 mm, greater than or equal to about 1.5 mm, or greater than or equal to about 3 mm. Combinations of the above-referenced ranges are also possible (e.g., greater than or equal to about 1 micron and less than or equal to about 1 mm). Other values of maximum cross-sectional dimensions are also possible.

In some cases, at least one or at least two cross-sectional dimensions (e.g., a height and a width) of a channel, channel segment, or channel portion may be less than or equal to about 2 mm, less than or equal to about 1 mm, less than or equal to about 750 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, or less than or equal to about 5 microns. In some instances, at least one or at least two cross-sectional dimensions of a channel, channel segment, channel portion, etc. may be greater than or equal to about 0.1 microns, greater than or equal to about 1 micron, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 400 microns, greater than or equal to about 600 microns, or greater than or equal to about 700 microns. Combinations of the above-referenced ranges are also possible (e.g., greater than or equal to about 10 μm and less than or equal to about 500 μm). Other values are also possible.

A channel, channel segment, or channel portion may have a certain width-to-height ratio. In certain instances, the ratio of the width to height of a channel, channel segment, or channel portion may be greater than or equal to about 1:1, greater than or equal to about 2:1, greater than or equal to about 5:1, greater than or equal to about 10:1, greater than or equal to about 15:1, or greater than or equal to about 20:1. In some instances the width-to-height ratio may be less than or equal to about 30:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

A channel, channel segment, or channel portion may also have an aspect ratio (length to largest average cross-sectional dimension) of at least 2:1, more typically at least 3:1, 5:1, or 10:1. In some cases, the channels, channel segments, or channel portions have very large aspect ratios, e.g., at least 100:1, 500:1 or 1000:1. Such long channels may be useful for mixing large volumes of fluids and/or large numbers of different fluid plugs in the channel. For instance, the channel, channel segment, or channel portion may contain greater than or equal to 3, 5, 10, 20, 30, or 50 fluid plugs (e.g., the fluid reagents and separating fluids being counted as different plugs). In certain embodiments, a channel, channel segment, or channel portion has a length to largest width of less than or equal to 10, 7, 5, 3, or 2. Short channels may be useful in certain devices for mixing smaller volumes of fluids.

A channel, channel segment, or channel portion may have a length and/or volume for mixing as described herein. In some embodiments a channel, channel segment, or channel portion may have a volume of greater than or equal to about 0.001 picoliters, greater than or equal to about 0.01 picoliters, greater than or equal to about 0.1 picoliters, greater than or equal to about 1 picoliters, greater than or equal to about 10 picoliters, greater than or equal to about 100 picoliters, greater than or equal to about 0.001 microliters, greater than or equal to about 0.01 microliters, greater than or equal to about 0.1 microliters, greater than or equal to about 1 microliter, greater than or equal to about 10 microliters, greater than or equal to about 25 microliters, greater than or equal to about 50 microliters, greater than or equal to about 100 microliters, greater than or equal to about 150, or greater than or equal to about 200 microliters. In some instances, a channel, channel segment, or channel portion may have a volume of less than or equal to about 250 microliters, less than or equal to about 200 microliters, less than or equal to about 150 microliters, less than or equal to about 100 microliters, less than or equal to about 50 microliters, less than or equal to about 25 microliters, less than or equal to about 15 microliters, less than or equal to about 10 microliters, less than or equal to about 5 microliters, less than or equal to about 1 microliters, less than or equal to about 0.1 microliters, or less than or equal to about 0.01 microliters, less than or equal to about 0.001 microliter, less than or equal to about 100 picoliter, less than or equal to about 10 picoliter, less than or equal to about 1 picoliter, or less than or equal to about 0.1 picoliter, less than or equal to about 0.01 picoliter. Combinations of the above-referenced ranges are also possible (e.g., greater than or equal to about 0.001 picoliters and less than or equal to about 200 microliters). Other volumes are also possible.

In some embodiments, a channel, channel segment, or channel portion may have a length of greater than or equal to about 1 mm, greater than or equal to about 5 mm, greater than or equal to about 10 mm, greater than or equal to about 20 mm, greater than or equal to about 40 mm, greater than or equal to about 60 mm, or greater than or equal to about 80 mm. In some instances, the length may be less than or equal to about 100 mm, less than or equal to about 90 mm, less than or equal to about 70 mm, less than or equal to about 50 mm, less than or equal to about 30 mm, or less than or equal to about 10 mm. Combinations of the above-referenced ranges are also possible (e.g., greater than or equal to about 1 mm and less than or equal to about 100 mm). Other values of length are also possible.

A channel, channel segment, or channel portion may have any suitable configuration. In some embodiments, a channel, channel segment, or channel portion may be a common channel, a branching channel, a channel segment on a side of a device that is separated from another channel segment by an intervening channel (e.g., a channel segment passing through the thickness of the device, as part of a two-sided device), or any other suitable configuration. In some cases, channel segments or channel portions may be separated from one another by a component (e.g., a vent valve or port), or may differ from one another based on a feature of the channel segment or portion (e.g., surface roughness, dimension, etc.). Other configurations are also possible.

A channel, channel segment, or channel portion can be covered or uncovered. In embodiments where it is covered, at least one portion of the channel can have a cross-section that is substantially enclosed, or the entire channel may be substantially enclosed along its entire length with the exception of its inlet(s) and outlet(s). One or more inlet(s) and/or outlet(s) may also be enclosed and/or sealed. In certain embodiments, one or more covers is adapted and arranged such that a channel segment, an inlet, and/or an outlet is substantially enclosed and/or sealed prior to first use of the device by a user, but opened or unsealed at first use. In some embodiments, such a configuration may substantially prevent fluids and/or other reagents stored in the device from being removed from the device (e.g., due to evaporation) during fabrication, shipping, and/or storage of the device, as described herein.

As used herein, "prior to first use" of the device means a time or times before the device is first used by an intended user after commercial sale. First use may include any step(s) requiring manipulation of the device by a user. For example, first use may involve one or more steps such as puncturing a sealed inlet or removing a cover from an inlet to introduce a reagent into the device, connecting two or more channels to cause fluid communication between the channels, preparation of the device (e.g., loading of reagents into the device) before analysis of a sample, loading of a sample onto or into the device, preparation of a sample in a region of the device, performing a reaction with a sample, detection of a sample, etc. First use, in this context, does not include manufacture or other preparatory or quality control steps taken by the manufacturer of the device. Those of ordinary skill in the art are well aware of the meaning of first use in this context, and will be able easily to determine whether a device of the invention has or has not experienced first use. In one set of embodiments, devices of the invention are disposable after first use, and it is particularly evident when such devices are first used, because it is typically impractical to use the devices at all after first use.

A fluidic device, or portions thereof, can be fabricated of any material suitable for forming a channel or other component. Non-limiting examples of materials include polymers (e.g., polyethylene, polystyrene, polymethylmethacrylate, polycarbonate, poly(dimethylsiloxane), PVC, PTFE, PET, and a cyclo-olefin copolymer), or metals including nickel, copper, stainless steel, bulk metallic glass, or other metals or alloys, or ceramics including glass, quartz, silica, alumina, zirconia, tungsten carbide, silicon carbide, or non-metallic materials such as graphite, silicon, or others. The material forming the fluidic device and any associated components (e.g., a cover) may be hard or flexible. Those of ordinary skill in the art can readily select suitable material(s) based upon e.g., its rigidity, its inertness to (e.g., freedom from degradation by) a fluid to be passed through it, its robustness at a temperature at which a particular device is to be used, its transparency/opacity to electromagnetic waves (e.g., light in the ultraviolet and visible regions, terahertz waves, microwaves, and so on), and/or the method used to fabricate features in the material. For instance, for injection molded or other extruded articles, the material used may include a thermoplastic (e.g., polypropylene, polystyrene, polyethylene, polymethylmethacrylate, cyclo-olefin copolymer, polycarbonate, acrylonitrile-butadiene-styrene, nylon 6, PVC, PTFE, PET), an elastomer (e.g., polyisoprene, isobutene-isoprene, nitrile, neoprene, ethylene-propylene, hypalon, silicone), a thermoset (e.g., epoxy, unsaturated polyesters, phenolics), or combinations thereof. In some embodiments, fluidic devices including two or more components or layers may be formed in different materials to tailor the components to the major function(s) of the each of the components, e.g., based upon the factors described herein.

In some embodiments, the material and dimensions (e.g., thickness) of a fluidic device (and/or cover of a device) are chosen such that it is substantially impermeable to water vapor. For instance, a fluidic device designed to store one or more fluids therein prior to first use may include a cover comprising a material known to provide a high vapor barrier, such as metal foil, certain polymers, certain ceramics and combinations thereof. In other cases, the material is chosen based at least in part on the shape and/or configuration of the fluidic device. For instance, certain materials can be used to form planar devices whereas other materials are more suitable for forming devices that are curved or irregularly shaped.

In some instances, a fluidic device is comprised of a combination of two or more materials, such as the ones listed above. For instance, channels of the fluidic device may be formed in polystyrene or other polymers (e.g., by injection molding) and a biocompatible tape may be used to seal the channels. The biocompatible tape or flexible material may include a material known to improve vapor barrier properties (e.g., metal foil, polymers or other materials known to have high vapor barriers), and may optionally allow access to inlets and outlets by puncturing or unpeeling the tape. A variety of methods can be used to seal a microfluidic channel or portions of a channel, or to join multiple layers of a device, including but not limited to, the use of adhesives, use adhesive tapes, gluing, bonding, welding, brazing, lamination of materials, or by mechanical methods (e.g., clamping, snapping mechanisms, etc.).

In some instances, a fluidic device comprises a combination of two or more separate components (e.g., layers or fluidic devices) mounted together. Independent channel networks, which may optionally include reagents stored and/or sealed therein prior to first use, may be included on or in the different components of the fluidic device. The separate components may be mounted together or otherwise associated with one another by any suitable means, such as by the methods described herein, e.g., to form a single (composite) fluidic device. In some embodiments, two or more channel networks are positioned in different components or layers of the fluidic device and are not connected fluidically prior to first use, but are connected fluidically at first use, e.g., by use of a fluidic connector, as described in more detail in U.S. Pat. No. 8,202,492, issued Jun. 19, 2012 (filed May 1, 2008) and entitled "Fluidic Connectors and Microfluidic Systems." In other embodiments, the two or more channel networks are connected fluidically prior to first use.

Advantageously, each of the different components or layers that form a composite fluidic device may be tailored individually depending on the designed function(s) of that component or layer. For example, in one set of embodiments, one component of a composite fluidic device may be tailored for storing wet reagents. In some such embodiments, that component may be formed in a material having a relatively low vapor permeability. Additionally or alternatively, e.g., depending on the amount of fluids to be stored, the storage region(s) of that fluidic device may be made with larger cross-sectional dimensions than channels or regions of other components not used for storage of liquids. The material used to form the fluidic device may be compatible with fabrication techniques suitable for forming larger cross-sectional dimensions. By contrast, a second component that may be tailored for detection of an analyte may, in some embodiments, include channel portions having smaller cross-sectional dimensions. Smaller cross-sectional dimensions may be useful, for example, in certain embodiments to allow more contact time between fluids flowing in the channel (e.g., a reagent solution or a wash fluid) and an analyte bound to a surface of the channel, for a given volume of fluid. Additionally or alternatively, a channel portion of the second component may have a lower surface roughness compared to a channel portion of another component. The smaller-cross sectional dimensions or lower surface roughness of the channel portions of the second component may, in certain embodiments, require a certain fabrication technique or fabrication tool different from that used to form a different component of the fluidic device. Furthermore, in some particular embodiments, the material used for the second component may be well characterized for protein attachment and detection. As such, it may be advantageous to form different channels segments used for different purposes on different components of a fluidic device, which can then be joined together prior to use by an intended user.

Additional characteristics and examples of fluidic devices and components thereof that can be combined with aspects described herein are described in more detail in U.S. Patent Publication No. 2011/0256551, filed Apr. 15, 2011 and entitled "Systems and Devices for Analysis of Samples," which is incorporated herein by reference in its entirety for all purposes.

The methods and systems described herein may involve variety of different types of analyses, and can be used to determine a variety of different samples. In some cases, an analysis involves a chemical and/or biological reaction. In some embodiments, a chemical and/or biological reaction involves binding. Different types of binding may take place in fluidic devices described herein. Binding may involve the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

In some embodiments, a chemical and/or biological reaction involves a reducing agent (e.g., hydroquinone, chlorohydroquinone, pyrogallol, metol, 4-aminophenol and phenidone, Fe(+2), Ti(+3), and V(+2)). In some cases, a chemical and/or biological reaction involves a metal precursor (e.g., a solution of a metal salt, such as a silver salt).

In some cases, a heterogeneous reaction (or assay) may take place in a fluidic device; for example, a binding partner may be associated with a surface of a channel, and the complementary binding partner may be present in the fluid phase. Other solid-phase assays that involve affinity reaction between proteins or other biomolecules (e.g., DNA, RNA, carbohydrates), or non-naturally occurring molecules, can also be performed. Non-limiting examples of typical reactions that can be performed in a fluidic device include chemical reactions, enzymatic reactions, immuno-based reactions (e.g., antigen-antibody), and cell-based reactions.

Non-limiting examples of analytes that can be determined (e.g., detected) using fluidic devices described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; autoantibodies; human and animal hormones, e.g., thyroid stimulating hormone (TSH), thyroxine (T4), vitamin D, vitamin B12, luteinizing hormone (LH), follicle-stimulating hormones (FSH), testosterone, progesterone, human chorionic gonadotropin, estradiol; other proteins or peptides, e.g. troponin I, troponin T, c-reactive protein, myoglobin, brain natriuretic protein, prostate specific antigen (PSA), free-PSA, complexed-PSA, pro-PSA, EPCA-2, PCADM-1, ABCA5, hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte.

In some embodiments, one or more reagents that can be used to determine an analyte of a sample (e.g., a binding partner of the analyte to be determined) is stored and/or sealed in a channel or chamber of a fluidic device prior to first use in order to perform a specific test or assay.

In cases where an antigen is being analyzed, a corresponding antibody or aptamer can be the binding partner associated with a surface of a microfluidic channel. If an antibody is the analyte, then an appropriate antigen or aptamer may be the binding partner associated with the surface. When a disease condition is being determined, it may be preferred to put the antigen on the surface and to test for an antibody that has been produced in the subject. Such antibodies may include, for example, antibodies to HIV.

In some embodiments, a fluidic device is adapted and arranged to perform an analysis involving accumulating an opaque material on a region of a channel segment, exposing the region to light, and determining the transmission of light through the opaque material. An opaque material may include a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than, for example, 90, 80, 70, 60, 50, 40, 30, 20, 10 or 1 percent of the light illuminating the opaque material. Examples of opaque materials include molecular layers of metal (e.g., elemental metal), ceramic layers, dyes, polymeric layers, and layers of an opaque substance (e.g., a dye). The opaque material may, in some cases, be a metal that can be electrolessly deposited. These metals may include, for example, silver, gold, copper, nickel, cobalt, palladium, and platinum. Precursors of these metals may be stored and/or flowed in the devices described herein.

An opaque material that forms in a channel may include a series of discontinuous independent particles that together form an opaque layer, but in one embodiment, is a continuous material that takes on a generally planar shape. The opaque material may have a dimension (e.g., a width of length) of, for example, greater than or equal to 1 micron, greater than or equal to 5 microns, greater than 10 microns, greater than or equal to 25 microns, or greater than or equal to 50 microns. In some cases, the opaque material extends across the width of the channel (e.g., a measurement zone) containing the opaque material. The opaque layer may have a thickness of, for example, less than or equal to 10 microns, less than or equal to 5 microns, less than or equal to 1 micron, less than or equal to 100 nanometers or less than or equal to 10 nanometers. Even at these small thicknesses, a detectable change in transmittance can be obtained. The opaque layer may provide an increase in assay sensitivity when compared to techniques that do not form an opaque layer.

In one set of embodiments, a fluidic device described herein is used for performing an immunoassay (e.g., for human IgG or PSA) and, optionally, uses silver enhancement for signal amplification. In such an immunoassay, after delivery of a sample (e.g., containing human IgG) to a reaction site or analysis region, binding between two components (e.g., between the human IgG and anti-human IgG) can take place. One or more reagents, which may be optionally stored in a channel of the device prior to use, can then flow over this binding pair complex. Optionally, one of the stored reagents may include a solution of metal colloid (e.g., a gold conjugated antibody) that specifically binds to the antigen to be detected (e.g., human IgG). In other embodiments, the metal colloid can be bound with the sample prior to arriving at the reaction site or analysis region. This metal colloid can provide a catalytic surface for the deposition of an opaque material, such as a layer of metal (e.g., silver), on a surface of the analysis region. The layer of metal can be formed by using a two component system: a metal precursor (e.g., a solution of silver salts) and a reducing agent (e.g., hydroquinone, chlorohydroquinone, pyrogallol, metol, 4-aminophenol and phenidone, Fe(+2), Ti(+3), and V(+2)), which can optionally be stored in different channels prior to use.

Mixing of the two reagents can be performed using the methods described herein (e.g., as shown illustratively in FIGS. 1-4). In other embodiments, as a positive or negative pressure differential is applied to the system, the silver salt and reducing solutions can merge at a channel intersection, where they mix (e.g., due to diffusion) in a channel, and then flow over the analysis region. If antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. An opaque layer that is formed in the channel can be detected optically, for example, by measuring a reduction in light transmittance through a portion of the analysis region (e.g., a serpentine channel region) compared to a portion of an area that does not include the antibody or antigen.

Alternatively, a signal can be obtained by measuring the variation of light transmittance as a function of time, as the film is being formed in an analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process) or magnetic signals (e.g., magnetic beads) can be used to allow detection of a signal by a detector.

Various types of fluids can be used with the fluidic devices described herein. As described herein, fluids may be introduced into the fluidic device at first use, and/or stored within the fluidic device prior to first use. Fluids include liquids such as solvents, solutions and suspensions. Fluids also include gases and mixtures of gases. The fluids may contain any suitable species such as a component for a chemical and/or biological reaction, a buffer, and/or a detecting agent. When multiple fluids are contained in a fluidic device, the fluids may be separated by another fluid that is preferably substantially immiscible in each of the first two fluids. For example, if a channel contains two different aqueous solutions, a separation plug of a third fluid may be substantially immiscible in both of the aqueous solutions. When aqueous solutions are to be kept separate, substantially immiscible fluids that can be used as separators may include gases such as air or nitrogen, or hydrophobic fluids that are substantially immiscible with the aqueous fluids. Fluids may also be chosen based at least in part on the fluid's reactivity with adjacent fluids, or based on other factors described herein. For example, an inert gas such as nitrogen may be used in some embodiments and may help preserve and/or stabilize any adjacent fluids. An example of an substantially immiscible liquid for separating aqueous solutions is perfluorodecalin.

The choice of a separator fluid may be made based on other factors as well, including any effect that the separator fluid may have on the surface tension of the adjacent fluid plugs. In some embodiments, it may be preferred to maximize the surface tension within any fluid plug to promote retention of the fluid plug as a single continuous unit under varying environmental conditions such as vibration, shock and temperature variations. Other factors relevant to mixing between fluids and fluid plugs can also be considered as described herein.

Separator fluids may also be inert to a reaction site (e.g., measurement zone) to which the fluids will be supplied. For example, if a reaction site includes a biological binding partner, a separator fluid such as air or nitrogen may have little or no effect on the binding partner. The use of a gas (e.g., air) as a separator fluid may also provide room for expansion within a channel of a fluidic device should liquids contained in the device expand or contract due to changes such as temperature (including freezing) or pressure variations.

A variety of determination (e.g., measuring, quantifying, detecting, and qualifying) techniques may be used, e.g., to analyze a sample component or other component or condition associated with a fluidic described herein. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. In other embodiments, determination techniques may measure conductivity or resistance. As such, an analyzer may be configured to include such and other suitable detection systems.

Different optical detection techniques provide a number of options for determining reaction (e.g., assay) results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. In some embodiments, a system may be operated with a minimum of optical devices (e.g., a simplified optical detector). For instance, the determining device may be free of a photomultiplier, may be free of a wavelength selector such as a grating, prism or filter, may be free of a device to direct or collimate light such as a collimator, or may be free of magnifying optics (e.g., lenses). Elimination or reduction of these features can result in a less expensive, more robust device.

Additional examples of detection systems are described in more detail below in U.S. Patent Publication No. 2011/0256551, filed Apr. 15, 2011 and entitled "Systems and Devices for Analysis of Samples," which is incorporated herein by reference in its entirety for all purposes.

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method" [H0498.70211WO00]; International Patent Publication No. WO2005/072858 (International Patent Application Serial No. PCT/US2005/003514), filed Jan. 26, 2005 and entitled "Fluid Delivery System and Method" [H0498.70219WO00]; International Patent Publication No. WO2006/113727 (International Patent Application Serial No. PCT/US06/14583), filed Apr. 19, 2006 and entitled "Fluidic Structures Including Meandering and Wide Channels" [H0498.70244WO00]; U.S. Pat. No. 8,202,492, issued Jun. 19, 2012 (filed May 1, 2008) and entitled "Fluidic Connectors and Microfluidic Systems" [C1256.70000US01]; U.S. Patent Publication No. 2009/0075390, filed Aug. 22, 2008, entitled "Liquid Containment for Integrated Assays" [C1256.70001US01]; U.S. Pat. No. 8,222,049, issued Jul. 17, 2012 (filed Apr. 25, 2008), entitled "Flow Control in Microfluidic Systems" [C1256.70002US01]; U.S. Pat. No. 8,221,700, issued Jul. 17, 2012 (filed Feb. 2, 2010), entitled "Structures for Controlling Light Interaction with Microfluidic Devices," [C1256.70003US01]; U.S. Patent Publication No. 2010/0158756, filed Dec. 17, 2009, entitled "Reagent Storage in Microfluidic Systems and Related Articles and Methods," [C1256.70004US01]; U.S. Patent Publication No. 2011/0120562, filed Nov. 24, 2010, entitled "Fluid Mixing and Delivery in Microfluidic Systems," [C1256.70005US01]; U.S. Patent Publication No. 2011/0253224, filed Apr. 15, 2011, entitled "Feedback Control in Microfluidic Systems," [C1256.70006US01]; U.S. Patent Publication No. 2011/0256551, filed Apr. 15, 2011, entitled "Systems and Devices for Analysis of Samples," [C1256.70010US01], each of which is incorporated herein by reference in its entirety for all purposes.

EXAMPLES

Example 1

This example shows the influence of channel geometry and surface tension of a fluid on volume reduction of a fluid plug during flow of the fluid plug in a channel.

Fluid plugs containing a fluid and varying concentrations of wetting agent were flowed through several channels that differed only in hydraulic diameter. The volume reduction of a fluid plug for a given channel length increased as the hydraulic diameter of the channel increased. The volume reduction for a given channel length also increased as the surface tension decreased (i.e., as the amount of wetting agent in the fluid plug increased). The effect of hydraulic diameter was less pronounced for fluids as the surface tension decreased.

Figure 8:
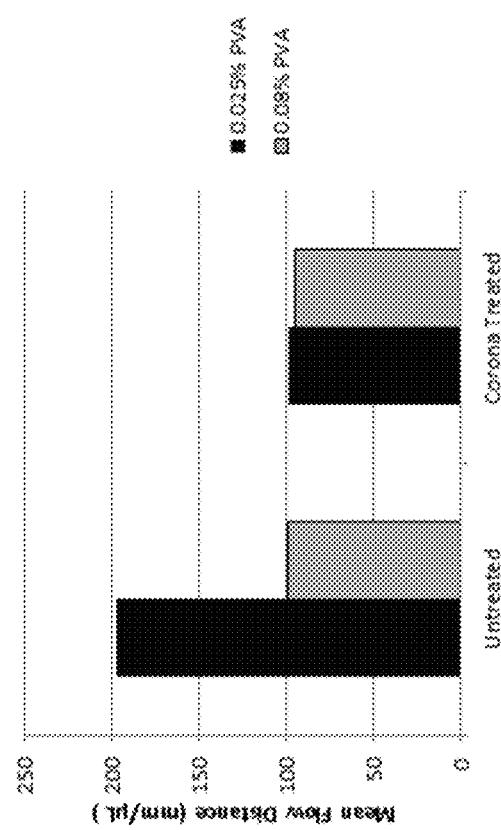
FIG. 8 shows a plot demonstrating the influence of treated and untreated channels on mixing according to one set of embodiments.

Three fluid plugs, varying only in the concentration of wetting agent, were flowed through channels with a hydraulic diameter of 0.4 mm to 1.0 mm. The distance required for complete volume reduction of each fluid plug (i.e., length of channel required to disperse the plug in mm per microliters) was recorded for each hydraulic diameter. Polyvinyl alcohol was used as the wetting agent to reduce the surface tension of the fluid. Each fluid plug contained 0.025% polyvinyl alcohol, 0.08% polyvinyl alcohol, or 0.4% polyvinyl alcohol in deionized water. FIG. 8 shows the distance required for each concentration of polyvinyl alcohol for each hydraulic diameter tested.

This example demonstrates that the volume reduction of a fluid plug (and, therefore, the amount of mixing between fluids) can be varied by tailoring the channel geometry and/or the surface tension of the fluid contained in the fluid plug.

Example 2

This example shows the influence of surface energy of the channel and surface tension of the fluid on volume reduction.

Figure 9:
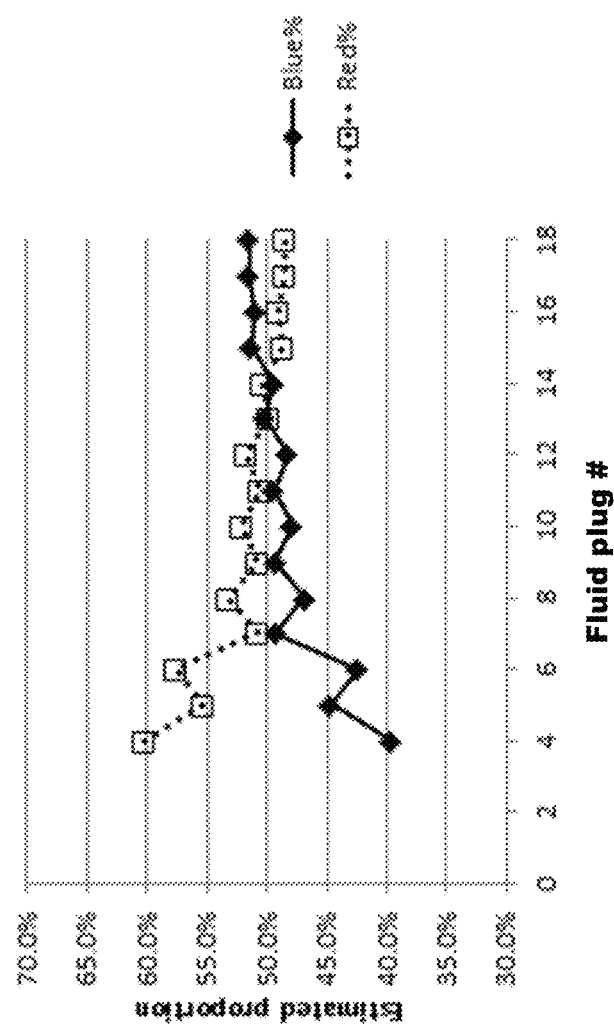
FIGS. 9-11 show plots of proportions of solutions after serial mixing between multiple fluids according to one set of embodiments.

Two identical channels with a height of 3.5 mm and a width of 0.5 mm were fabricated. One channel was treated with atmospheric corona discharge to increase the surface energy of the channel. A corona discharge was applied for about 1 second at a distance of 1 cm away from the surface of the channel. The corona discharge treatment produced a surface energy of greater than 72 dynes/cm as indicated by deionized water spreading into a film rather than beading up. Polyvinyl alcohol was used as the wetting agent to reduce the surface tension of the fluid. The fluid plugs contained either 0.025% polyvinyl alcohol or 0.08% polyvinyl alcohol in deionized water. FIG. 9 shows the length of channel required for complete volume reduction of the fluid plug for each concentration of polyvinyl alcohol for the untreated and the corona-treated channel.

Two channels that differed only in their surface energy were formed. Fluid plugs containing a fluid and varying concentrations of wetting agent were flowed through the two channels. The volume reduction of a fluid plug, for a given channel length, increased as surface energy increased. The volume reduction, for a given channel length, also increased as the surface tension decreased (i.e., as the amount of wetting agent in the fluid plug increased). The effect of surface energy was less pronounced with decreased surface tension. In addition, the effect of surface tension was less pronounced with increased surface energy.

The corona treated channel had about a 50% decrease in mean length of channel required to disperse the plug compared to the untreated channel for a fluid plug with 0.025% polyvinyl alcohol. Decreasing the surface tension of the fluid caused about a 50% decrease in mean length of channel required to disperse the plug in the untreated channel.

This example demonstrates that the volume reduction of a fluid plug (and, therefore, the amount of mixing between fluids) can be varied by tailoring the surface energy of the channel containing the fluid plug, and/or the surface tension of the fluid contained in the fluid plug.

Example 3

This example shows serial mixing of multiple fluid plugs in a channel.

A microfluidic channel was loaded with fluid plugs containing air or a solution of deionized water containing 5 mg/mL of a blue dye (methylene blue) or 10 mg/mL of a red dye (allura red). The aqueous fluid plugs were immiscible with the air fluid plugs. The fluid plugs alternated between aqueous fluid plugs and air fluid plugs. The aqueous fluid plugs alternated in dye color, such that the first aqueous fluid plug contained a red dye, the second contained a blue dye, third contained a red dye, etc. The channel contained nine fluid plugs of each dye color. Each aqueous fluid plug had a volume of 2 µL. Mixing was initiated by connecting a vacuum of approximately 30 kPa to the outlet of the system. From the outlet, the mixed solutions flowed through a microfluidic channel in which the optical density of the solutions was measured with red and green light as described below. The ratio of red dye to blue dye in the fluid plugs after flowing in the channel could be calculated from these measurements using the regression model described above.

The optical densities of the aqueous fluid plugs were measured after following in the channel. An LED emitting either red (~630 nm) or green (~505 nm) light was positioned above the channel, while an optical detector was positioned below the channel, and the optical transmission through the channel was monitored and recorded using a data capture system. The optical density was calculated using the optical transmission of deionized water without any dye as a reference value. Various solutions containing known concentrations of red dye, blue dye, or a mixture of the two were flowed through the system, and the optical density was measured with red and green light. A multivariate regression model was fit to these results to permit estimation of the dye concentration in mixed solutions based on the optical density measured with red and green light. This model was used in the experiments described herein.

Figure 10:
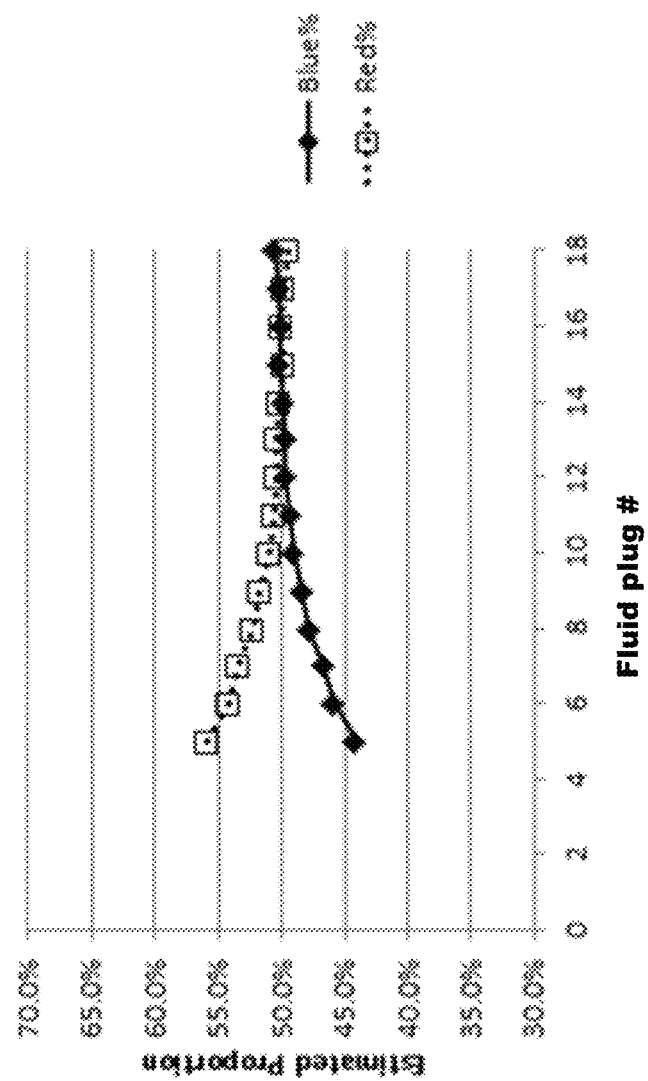

Mixing of multiple fluid plugs was shown using aqueous fluid plugs differing only in the presence of either a red dye or a blue dye. The aqueous fluid plugs alternated in dye color and were separated by fluid plugs containing air. The fluid plugs were flowed in a microfluidic channel. The ratios of red and blue dye in each aqueous fluid plug were measured after flowing in the microfluidic channel for about 350 mm (i.e., the first plug was 350 mm away from their initial positions). The first three aqueous fluid plugs were completely dissipated along the channel wall, as indicated by the absence of any data points in fluid plug #s 1-3 in FIG. 10, and were absorbed by the subsequent aqueous fluid plugs. After the sixth aqueous fluid plug, the percent of red dye and blue dye in each aqueous fluid plug was within 50%±5% which was the initial overall percentage of red and blue dye in the channel. FIG. 10 shows a plot of the percent of the red and blue dye in each aqueous fluid plug calculated from their measured optical densities after flowing in the microfluidic system. The overall enrichment of red solution in the earlier segments is attributed to the fact that the first and third aqueous fluid plugs were red.

This example demonstrates that serial mixing can be performed with multiple fluid plugs in a channel. This example also demonstrates that the ratio of components in the fluid plugs after mixing converges toward the initial overall ratio of components in the total volume loaded into the channel.

Example 4

This example shows the influence of surface roughness and channel length on mixing of multiple fluid plugs.

Mixing of multiple fluid plugs was performed with an identical set-up as Example 3, except the microfluidic channel had an additional length of 630 mm and the additional channel length had been treated with micro-abrasive blasting to change the surface texture. Roughness was measured by stylus profilometry with a stylus tip radius of approximately 2 µm. The channel had an average roughness between about 0.1 µm and 0.5 µm. The first four aqueous fluid plugs were completely dissipated along the channel wall. After the fifth aqueous fluid plug, the ratio of red dye to blue dye in the aqueous fluid plugs was about 50:50, which was the initial overall ratio of red dye to blue dye.

Figure 11:
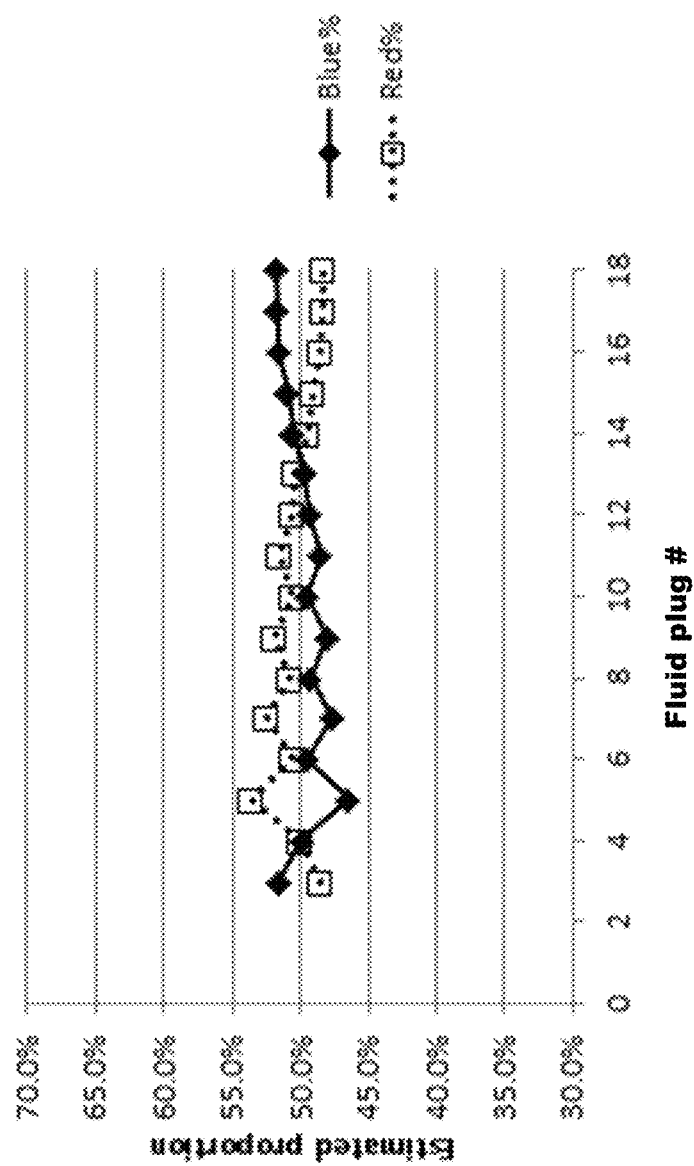

FIG. 11 shows a plot of the percent of the red and blue dye in each aqueous fluid plug calculated from their measured optical densities after flowing in the microfluidic system. The first four aqueous fluid plugs were distributed along the channel, and were absorbed by the subsequent aqueous fluid plugs. After the fifth aqueous fluid plug, the percent of red dye and blue dye was within 50%±5% in each fluid plug. The overall enrichment of red solution in the earlier segments is attributed to the fact that the first and third aqueous fluid plugs were red.

This example demonstrates that surface roughness can be used to increase fluid dissipation and enhance mixing in a channel.

Example 5

This example shows the influence of volume of the fluid plugs on mixing of multiple fluid plugs.

Mixing of multiple fluid plugs was performed with an identical set-up as Example 3, except the first aqueous fluid plug had a volume of 1 microliter. The first and second aqueous fluid plugs were completely dissipated along the channel wall. After the second aqueous fluid plug, the ratio of red dye to blue dye in the aqueous fluid plugs was about 50:50.

FIG. 12 shows a plot of the percent of the red and blue dye in each aqueous fluid plug calculated from their measured optical densities after flowing in the microfluidic channel. The first and second aqueous fluid plugs were entirely dissipated along the channel, and were absorbed by the subsequent aqueous fluid plugs. After the second aqueous fluid plug, the percent of red dye and blue dye in each fluid plug was within 50%±5%.

This example demonstrates that the ratio of components in each fluid plug after mixing is dependent upon the volume of the fluid plugs carrying the fluids to be mixed.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method, comprising:
flowing in a channel a series of fluid plugs comprising a first fluid plug comprising a first fluid, a second fluid plug comprising a second fluid, and a third fluid plug comprising a third fluid, wherein the first fluid plug has a first volume,
wherein the second fluid plug is positioned between the first and third fluid plugs, and
wherein the second fluid is immiscible with each of the first and third fluids,
wherein prior to the flowing step, the channel comprises a reagent that is dry, the method comprising:
contacting the first and/or third fluid with the reagent;
while the first fluid plug is flowing, depositing at least a portion of the first fluid on a wall of the channel for combining with the third fluid plug;
reducing the first volume of the first fluid plug by at least 50%;
combining at least a portion of the first fluid into the third fluid plug so as to mix at least portions of the first and third fluids; and
after the combining step, flowing in the channel the first fluid plug, the second fluid plug, and the third fluid plug which comprises the third fluid and at least a portion of the first fluid.

2. A method as in claim 1, comprising contacting the reagent with the first and/or third fluid, and performing a chemical and/or biological reaction and/or a binding event between the reagent and an at least one component of the first and/or third fluid.

3. A method as in claim 1, comprising reducing the first volume of the first fluid plug by at least 75%.

4. A method as in claim 1, wherein after the step of flowing in the channel the first fluid plug, the second fluid plug, and the third fluid plug which comprises the third fluid and at least a portion of the first fluid, the method comprises reducing the first volume of the first fluid plug by 100%.

5. A method as in claim 1, wherein the first fluid and the third fluid are miscible with one another.

6. A method as in claim 1, wherein the first fluid plug comprises a first component and the third fluid plug comprises a second component, the method comprising performing one or more chemical and/or biological reactions and/or binding events involving each of the first and second components.

7. A method as in claim 6, comprising performing a chemical and/or biological reaction and/or a binding event between the first and second components.

8. A method as in claim 1, flowing in series a fourth fluid plug comprising a fourth fluid and a fifth fluid plug comprising a fifth fluid along with the first, second and third fluid plugs, wherein the fourth fluid is immiscible with the first, third and fifth fluids.

9. A method as in claim 1, comprising reducing the volume of the third fluid plug.

10. A method as in claim 1, comprising reducing the volume of the third fluid plug by at least 50%.

11. A method as in claim 8, comprising combining at least a portion of the third fluid into the fifth fluid plug so as to mix at least portions of the third and fifth fluids.

12. A method as in claim 1, comprising depositing at least a portion of the first fluid on a wall of the channel during the step of flowing the first, second and third fluid plugs in series.

13. A method as in claim 12, wherein the first fluid is deposited as a film on the wall of the channel.

14. A method as in claim 12, wherein the first fluid is deposited as fluid droplets on the wall of the channel.

15. A method as in claim 1, wherein the first and/or third fluid comprises a metal salt.

16. A method as in claim 1, wherein the second fluid comprises a gas.

17. A method as in claim 1, wherein the second fluid is hydrophobic.

18. A method as in claim 1, wherein the second fluid is directly adjacent the first and third fluids.

19. A method as in claim 1, wherein the channel has a cross-section comprising a radius of curvature smaller than the half-width of the channel.

20. A method as in claim 1, wherein the channel has a cross-section comprising a radius of curvature smaller than the half-height of the channel.

21. A method as in claim 1, wherein the channel has an average diameter of less than or equal to 1 mm.

22. A method as in claim 1, wherein the combining step is performed while the first, second, and third fluid plugs are flowing in series from an upstream portion to a downstream portion of the channel.

23. A method as in claim 1, wherein after the combining step, the first, second, and third fluid plugs are flowed in series from an upstream portion to a downstream portion of the channel.

24. A method as in claim 1, wherein the first and/or third fluid comprises a wetting agent.

25. A method as in claim 1, wherein the combining step occurs while the first fluid plug, the second fluid plug, and the third fluid plug are flowing in series.

26. A method as in claim 1, wherein the channel is configured to remove at least a portion of the first fluid from the first fluid plug and deposit at least a portion of the first fluid on a wall of the channel during the step of flowing.

* * * * *